United States Patent
Kolb et al.

(10) Patent No.: US 8,608,746 B2
(45) Date of Patent: Dec. 17, 2013

(54) DEROTATION INSTRUMENT WITH REDUCTION FUNCTIONALITY

(75) Inventors: Eric Kolb, Milton, MA (US); Thomas J. Runco, Providence, RI (US); Richard Fournier, New Bedford, MA (US); James R. Donahue, East Falmouth, MA (US); Shawn Stad, Fall River, MA (US)

(73) Assignee: Depuy Synthes Products, LLC, Raynham, MA (US)

( * ) Notice: Subject to any disclaimer, the term of this patent is extended or adjusted under 35 U.S.C. 154(b) by 578 days.

(21) Appl. No.: 12/075,412

(22) Filed: Mar. 10, 2008

(65) Prior Publication Data
US 2009/0228053 A1    Sep. 10, 2009

(51) Int. Cl.
*A61B 17/88* (2006.01)

(52) U.S. Cl.
USPC ........................................... 606/86 A

(58) Field of Classification Search
USPC ................. 606/86 R, 86 A, 247–279
See application file for complete search history.

(56) References Cited

U.S. PATENT DOCUMENTS

| | | | |
|---|---|---|---|
| 410,780 A | 9/1889 | Cahn | |
| 445,513 A | 1/1891 | Powell | |
| 1,470,313 A | 10/1923 | Woolen | |
| 1,628,144 A | 5/1927 | Herrmann | |
| 1,709,766 A | 4/1929 | Bolton | |
| 1,889,330 A | 11/1932 | Humes et al. | |
| 1,925,385 A | 9/1933 | Humes, et al. | |
| 2,113,246 A | 4/1938 | Frederick | |
| 2,248,054 A | 7/1941 | Becker | |
| 2,248,057 A | 7/1941 | Bond | |
| 2,291,413 A | 7/1942 | Siebrandt | |
| 2,370,407 A | 2/1945 | Howard | |
| 2,669,896 A | 2/1954 | Clough | |
| 2,800,820 A | 7/1957 | Retterath | |
| 2,952,285 A | 9/1960 | Roosli | |
| 3,604,487 A | 9/1971 | Gilbert | |
| 3,960,147 A | 6/1976 | Murray | |
| 4,237,875 A | 12/1980 | Termanini | |
| 4,271,836 A | 6/1981 | Bacal et al. | |
| 4,363,250 A | 12/1982 | Suga | |
| 4,411,259 A | 10/1983 | Drummond | |
| 4,445,513 A | 5/1984 | Ulrich et al. | |

(Continued)

FOREIGN PATENT DOCUMENTS

| | | |
|---|---|---|
| DE | 3923996 A1 | 1/1991 |
| DE | 4107480 A1 | 9/1992 |

(Continued)

OTHER PUBLICATIONS

International Search Report and Written Opinion for Application No. PCT/US09/36343, dated Jan. 7, 2010.

(Continued)

*Primary Examiner* — Mary Hoffman
*Assistant Examiner* — Tara Carter
(74) *Attorney, Agent, or Firm* — Nelson Mullins Riley & Scarborough LLP

(57) ABSTRACT

Instruments and methods are provided for manipulating a bone anchor and a spinal fixation element. The instruments and methods disclosed herein are particularly suited to facilitate rotation of a bone anchor relative to another bone to correct the angular rotation of the vertebrae attached to the bone anchor. The instrument does not require the spinal fixation element to be inserted into the bone anchor prior to manipulation. The instrument further may be used in the insertion of the spinal fixation element into the bone anchor.

18 Claims, 17 Drawing Sheets

(56) References Cited

U.S. PATENT DOCUMENTS

| | | |
|---|---|---|
| 4,655,223 A | 4/1987 | Kim |
| 4,733,657 A | 3/1988 | Kluger |
| 4,743,260 A | 5/1988 | Burton |
| 4,809,695 A | 3/1989 | Gwathmey et al. |
| 4,887,596 A | 12/1989 | Sherman |
| 4,896,661 A | 1/1990 | Bogert et al. |
| 4,957,495 A | 9/1990 | Kluger et al. |
| 4,987,892 A | 1/1991 | Krag et al. |
| 5,005,562 A | 4/1991 | Cotrel et al. |
| 5,014,407 A | 5/1991 | Boughten et al. |
| 5,020,519 A | 6/1991 | Hayes et al. |
| 5,067,955 A | 11/1991 | Cotrel |
| 5,092,866 A | 3/1992 | Breard et al. |
| 5,120,171 A | 6/1992 | Lasner |
| 5,176,678 A | 1/1993 | Tsou |
| 5,176,680 A | 1/1993 | Vignaud et al. |
| 5,181,917 A | 1/1993 | Rogozinski |
| 5,181,971 A | 1/1993 | Ohtsuka |
| 5,190,543 A | 3/1993 | Schlapfer |
| 5,219,349 A | 6/1993 | Krag et al. |
| 5,226,766 A | 7/1993 | Lasner |
| 5,263,939 A | 11/1993 | Wortrich |
| 5,282,801 A | 2/1994 | Sherman |
| 5,282,863 A | 2/1994 | Burton |
| D346,217 S | 4/1994 | Sparker et al. |
| 5,306,248 A | 4/1994 | Barrington |
| 5,330,474 A | 7/1994 | Lin |
| 5,360,431 A | 11/1994 | Puno et al. |
| 5,364,397 A | 11/1994 | Hayes et al. |
| 5,385,565 A | 1/1995 | Ray |
| 5,387,213 A | 2/1995 | Breard et al. |
| 5,391,170 A | 2/1995 | McGuire et al. |
| 5,415,661 A | 5/1995 | Holmes |
| 5,429,641 A | 7/1995 | Gotfried |
| 5,468,241 A | 11/1995 | Metz-Stavenhagen et al. |
| 5,478,340 A | 12/1995 | Kluger |
| 5,484,440 A | 1/1996 | Allard |
| 5,487,744 A | 1/1996 | Howland |
| 5,499,983 A | 3/1996 | Hughes |
| 5,501,684 A | 3/1996 | Schlapfer et al. |
| 5,520,689 A | 5/1996 | Schlapfer et al. |
| 5,536,127 A | 7/1996 | Pennig |
| 5,536,268 A | 7/1996 | Griss |
| 5,540,688 A | 7/1996 | Navas |
| 5,545,165 A | 8/1996 | Biedermann et al. |
| 5,549,608 A | 8/1996 | Errico et al. |
| 5,551,320 A | 9/1996 | Horobec et al. |
| 5,591,166 A | 1/1997 | Bernhardt et al. |
| 5,616,143 A | 4/1997 | Schlapfer et al. |
| 5,649,931 A | 7/1997 | Bryant et al. |
| 5,667,513 A | 9/1997 | Torrie et al. |
| 5,672,175 A | 9/1997 | Martin |
| 5,672,176 A | 9/1997 | Biedermann et al. |
| 5,683,399 A | 11/1997 | Jones |
| 5,697,933 A | 12/1997 | Gundlapalli et al. |
| 5,707,371 A | 1/1998 | Metz-Stavenhagen |
| 5,720,751 A | 2/1998 | Jackson |
| 5,725,532 A | 3/1998 | Shoemaker |
| 5,746,757 A | 5/1998 | McGuire |
| 5,782,831 A | 7/1998 | Sherman et al. |
| 5,797,910 A | 8/1998 | Martin |
| 5,797,911 A | 8/1998 | Sherman et al. |
| 5,810,878 A | 9/1998 | Burel et al. |
| 5,814,046 A | 9/1998 | Hopf |
| 5,879,350 A | 3/1999 | Sherman et al. |
| 5,882,350 A | 3/1999 | Ralph et al. |
| 5,885,285 A | 3/1999 | Simonson |
| RE36,211 E | 5/1999 | Nonomura |
| RE36,221 E | 6/1999 | Breard et al. |
| 5,910,141 A | 6/1999 | Morrison et al. |
| 5,941,885 A | 8/1999 | Jackson |
| 5,951,555 A | 9/1999 | Rehak et al. |
| 5,951,564 A | 9/1999 | Schroder et al. |
| 5,951,579 A | 9/1999 | Dykes |
| 5,964,760 A | 10/1999 | Richelsoph |
| 5,976,133 A | 11/1999 | Kraus et al. |
| 5,989,250 A | 11/1999 | Wagner et al. |
| 5,989,254 A | 11/1999 | Katz |
| 6,010,509 A | 1/2000 | Delgado et al. |
| 6,036,692 A | 3/2000 | Burel et al. |
| 6,050,997 A | 4/2000 | Mullane |
| 6,063,090 A | 5/2000 | Schlapfer |
| 6,074,391 A | 6/2000 | Metz-Stavenhagen et al. |
| 6,090,110 A | 7/2000 | Metz-Stavenhagen |
| 6,090,113 A | 7/2000 | Le Couedic et al. |
| 6,099,528 A | 8/2000 | Saurat |
| 6,123,707 A | 9/2000 | Wagner |
| 6,139,549 A | 10/2000 | Keller |
| 6,146,383 A | 11/2000 | Studer et al. |
| 6,183,472 B1 | 2/2001 | Lutz |
| 6,189,422 B1 | 2/2001 | Stihl |
| 6,204,060 B1 | 3/2001 | Mehtali et al. |
| 6,210,330 B1 | 4/2001 | Tepper |
| 6,235,028 B1 | 5/2001 | Brumfield et al. |
| 6,251,112 B1 | 6/2001 | Jackson |
| 6,254,602 B1 | 7/2001 | Justis |
| 6,258,090 B1 | 7/2001 | Jackson |
| 6,261,287 B1 | 7/2001 | Metz-Stavenhagen |
| 6,280,442 B1 | 8/2001 | Barker et al. |
| 6,280,443 B1 | 8/2001 | Gu et al. |
| 6,299,616 B1 | 10/2001 | Beger |
| 6,302,888 B1 | 10/2001 | Mellinger et al. |
| 6,309,389 B1 | 10/2001 | Baccelli |
| 6,368,321 B1 | 4/2002 | Jackson |
| 6,371,973 B1 | 4/2002 | Tepper |
| 6,379,357 B1 | 4/2002 | Bernstein et al. |
| 6,423,065 B2 | 7/2002 | Ferree |
| 6,440,133 B1 | 8/2002 | Beale et al. |
| 6,440,137 B1 | 8/2002 | Horvath et al. |
| 6,440,142 B1 | 8/2002 | Ralph et al. |
| 6,440,144 B1 | 8/2002 | Bacher |
| 6,443,953 B1 | 9/2002 | Perra et al. |
| 6,478,798 B1 | 11/2002 | Howland |
| 6,511,484 B2 | 1/2003 | Torode et al. |
| 6,530,929 B1 | 3/2003 | Justis et al. |
| 6,540,748 B2 | 4/2003 | Lombardo |
| 6,565,567 B1 | 5/2003 | Haider |
| 6,589,249 B2 | 7/2003 | Sater et al. |
| 6,597,279 B2 | 7/2003 | Haraguchi |
| 6,623,485 B2 | 9/2003 | Doubler et al. |
| 6,648,888 B1 | 11/2003 | Shluzas |
| 6,652,523 B1 | 11/2003 | Evrard et al. |
| 6,660,006 B2 | 12/2003 | Markworth et al. |
| 6,689,137 B2 | 2/2004 | Reed |
| 6,692,500 B2 | 2/2004 | Reed |
| 6,695,843 B2 | 2/2004 | Biedermann et al. |
| 6,716,214 B1 | 4/2004 | Jackson |
| 6,726,692 B2 | 4/2004 | Bette et al. |
| 6,733,502 B2 | 5/2004 | Altarac et al. |
| 6,743,231 B1 | 6/2004 | Gray et al. |
| 6,746,449 B2 | 6/2004 | Jones et al. |
| 6,749,613 B1 | 6/2004 | Conchy et al. |
| 6,752,832 B2 | 6/2004 | Neumann |
| 6,755,829 B1 | 6/2004 | Bono et al. |
| 6,783,527 B2 | 8/2004 | Drewry et al. |
| 6,790,208 B2 | 9/2004 | Oribe et al. |
| 6,790,209 B2 | 9/2004 | Beale et al. |
| 6,800,078 B2 | 10/2004 | Reed |
| 6,800,079 B2 | 10/2004 | Reed |
| 6,827,722 B1 | 12/2004 | Schoenefeld |
| 6,837,889 B2 | 1/2005 | Shluzas |
| 6,964,666 B2 | 11/2005 | Jackson |
| 7,083,621 B2 | 8/2006 | Shaolian et al. |
| 7,156,849 B2 | 1/2007 | Dunbar et al. |
| 7,160,300 B2 | 1/2007 | Jackson |
| 7,179,254 B2 | 2/2007 | Pendekanti et al. |
| 7,179,261 B2 | 2/2007 | Sicvol et al. |
| 7,250,052 B2 | 7/2007 | Landry et al. |
| 7,278,995 B2 | 10/2007 | Nichols et al. |
| 7,320,689 B2 | 1/2008 | Keller |
| 7,322,979 B2 | 1/2008 | Crandall et al. |
| 7,371,239 B2 | 5/2008 | Dec et al. |
| 7,455,685 B2 | 11/2008 | Justis |
| 7,462,182 B2 | 12/2008 | Lim |

(56) References Cited

U.S. PATENT DOCUMENTS

| | | |
|---|---|---|
| 7,465,306 B2 | 12/2008 | Pond, Jr. et al. |
| 7,470,279 B2 | 12/2008 | Jackson |
| 7,485,120 B2 | 2/2009 | Ray |
| 7,491,207 B2 | 2/2009 | Keyer et al. |
| 7,491,208 B2 | 2/2009 | Pond, Jr. et al. |
| 7,491,218 B2 | 2/2009 | Landry et al. |
| 7,527,638 B2 | 5/2009 | Anderson et al. |
| 7,572,281 B2 | 8/2009 | Runco et al. |
| 7,588,585 B2 | 9/2009 | Gold et al. |
| 7,591,836 B2 | 9/2009 | Dick et al. |
| 7,621,918 B2 | 11/2009 | Jackson |
| 7,651,502 B2 | 1/2010 | Jackson |
| 7,666,188 B2 | 2/2010 | Anderson et al. |
| 7,666,189 B2 | 2/2010 | Gerber et al. |
| 7,708,736 B2 | 5/2010 | Mullaney |
| 7,708,763 B2 | 5/2010 | Selover et al. |
| 7,766,944 B2 | 8/2010 | Metz-Stavenhagen |
| 7,794,464 B2 | 9/2010 | Bridwell et al. |
| 7,867,237 B2 | 1/2011 | Stad et al. |
| 7,887,539 B2 | 2/2011 | Dunbar, Jr. et al. |
| 7,887,541 B2 | 2/2011 | Runco et al. |
| 7,951,168 B2 | 5/2011 | Chao et al. |
| 7,951,172 B2 | 5/2011 | Chao et al. |
| 7,951,175 B2 | 5/2011 | Chao et al. |
| 7,988,698 B2 | 8/2011 | Rosenberg et al. |
| 8,007,516 B2 | 8/2011 | Chao et al. |
| 8,172,847 B2 | 5/2012 | Dziedzic et al. |
| 2001/0020169 A1 | 9/2001 | Metz-Stavenhagen |
| 2001/0029376 A1 | 10/2001 | Sater et al. |
| 2002/0035366 A1 | 3/2002 | Walder et al. |
| 2002/0082599 A1 | 6/2002 | Crandall et al. |
| 2002/0095153 A1 | 7/2002 | Jones et al. |
| 2002/0133155 A1 | 9/2002 | Ferree |
| 2002/0143341 A1 | 10/2002 | Biedermann et al. |
| 2002/0173789 A1 | 11/2002 | Howland |
| 2003/0009168 A1 | 1/2003 | Beale et al. |
| 2003/0028195 A1 | 2/2003 | Bette |
| 2003/0073995 A1 | 4/2003 | Reed |
| 2003/0083657 A1 | 5/2003 | Drewry et al. |
| 2003/0083747 A1 | 5/2003 | Winterbottom et al. |
| 2003/0088248 A1 | 5/2003 | Reed |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125750 A1 | 7/2003 | Zwimmann et al. |
| 2003/0149438 A1 | 8/2003 | Nichols et al. |
| 2003/0171749 A1 | 9/2003 | Le Couedic et al. |
| 2003/0176861 A1 | 9/2003 | Reed |
| 2003/0191370 A1 | 10/2003 | Phillips |
| 2003/0191470 A1 | 10/2003 | Ritland |
| 2003/0199872 A1 | 10/2003 | Markworth et al. |
| 2003/0203488 A1 | 10/2003 | Mehtali et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2004/0002708 A1 | 1/2004 | Ritland |
| 2004/0036254 A1 | 2/2004 | Patton |
| 2004/0049189 A1 | 3/2004 | Le Couedic et al. |
| 2004/0049190 A1 | 3/2004 | Biedermann et al. |
| 2004/0049191 A1 | 3/2004 | Markworth et al. |
| 2004/0073215 A1 | 4/2004 | Carli |
| 2004/0102789 A1 | 5/2004 | Baughman |
| 2004/0147936 A1 | 7/2004 | Rosenberg et al. |
| 2004/0147937 A1 | 7/2004 | Dunbar et al. |
| 2004/0158257 A1 | 8/2004 | Bonati et al. |
| 2004/0158258 A1 | 8/2004 | Bonati et al. |
| 2004/0172025 A1 | 9/2004 | Drewry et al. |
| 2004/0172057 A1 | 9/2004 | Guillebon et al. |
| 2004/0176779 A1 | 9/2004 | Casutt et al. |
| 2004/0181224 A1 | 9/2004 | Biedermann et al. |
| 2004/0186473 A1 | 9/2004 | Cournoyer et al. |
| 2004/0204711 A1 | 10/2004 | Jackson |
| 2004/0220567 A1 | 11/2004 | Eisermann et al. |
| 2004/0225289 A1 | 11/2004 | Biedermann et al. |
| 2004/0243139 A1 | 12/2004 | Lewis et al. |
| 2004/0254576 A1 | 12/2004 | Dunbar et al. |
| 2004/0267260 A1 | 12/2004 | Mack et al. |
| 2004/0267275 A1 | 12/2004 | Cournoyer et al. |
| 2005/0015095 A1 | 1/2005 | Keller |
| 2005/0033291 A1 | 2/2005 | Ebara |
| 2005/0033295 A1 | 2/2005 | Wisnewski |
| 2005/0033299 A1 | 2/2005 | Shluzas |
| 2005/0055031 A1 | 3/2005 | Lim |
| 2005/0059969 A1 | 3/2005 | McKinley |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070917 A1 | 3/2005 | Justis |
| 2005/0079909 A1 | 4/2005 | Singhaseni |
| 2005/0085813 A1 | 4/2005 | Spitler et al. |
| 2005/0085815 A1 | 4/2005 | Harms et al. |
| 2005/0090824 A1 | 4/2005 | Shluzas et al. |
| 2005/0131408 A1 | 6/2005 | Sicvol et al. |
| 2005/0131420 A1 | 6/2005 | Techiera et al. |
| 2005/0131421 A1 | 6/2005 | Anderson et al. |
| 2005/0131422 A1 | 6/2005 | Anderson et al. |
| 2005/0137593 A1 | 6/2005 | Gray et al. |
| 2005/0143749 A1 | 6/2005 | Zalenski et al. |
| 2005/0149036 A1 | 7/2005 | Varieur et al. |
| 2005/0149048 A1 | 7/2005 | Leport et al. |
| 2005/0149053 A1 | 7/2005 | Varieur et al. |
| 2005/0154389 A1 | 7/2005 | Selover et al. |
| 2005/0159650 A1 | 7/2005 | Raymond et al. |
| 2005/0177163 A1 | 8/2005 | Abdou |
| 2005/0192570 A1 | 9/2005 | Jackson |
| 2005/0192573 A1 | 9/2005 | Abdelgany et al. |
| 2005/0192579 A1 | 9/2005 | Jackson |
| 2005/0192589 A1 | 9/2005 | Raymond et al. |
| 2005/0222570 A1 | 10/2005 | Jackson |
| 2005/0228376 A1 | 10/2005 | Boomer et al. |
| 2005/0228380 A1 | 10/2005 | Moore et al. |
| 2005/0228392 A1 | 10/2005 | Keyer et al. |
| 2005/0228400 A1 | 10/2005 | Chao et al. |
| 2005/0234449 A1 | 10/2005 | Aferzon |
| 2005/0245928 A1 | 11/2005 | Colleran et al. |
| 2005/0261687 A1 | 11/2005 | Garamszegi et al. |
| 2005/0261702 A1 | 11/2005 | Oribe et al. |
| 2005/0283244 A1 | 12/2005 | Gordon |
| 2005/0288668 A1 | 12/2005 | Brinkhaus |
| 2006/0009775 A1 | 1/2006 | Dec et al. |
| 2006/0025768 A1 | 2/2006 | Iott et al. |
| 2006/0036254 A1 | 2/2006 | Lim |
| 2006/0036255 A1 | 2/2006 | Pond et al. |
| 2006/0036260 A1 | 2/2006 | Runco et al. |
| 2006/0069391 A1 | 3/2006 | Jackson |
| 2006/0074418 A1 | 4/2006 | Jackson |
| 2006/0079909 A1 | 4/2006 | Runco et al. |
| 2006/0089651 A1 | 4/2006 | Trudeau et al. |
| 2006/0095035 A1 | 5/2006 | Jones et al. |
| 2006/0111712 A1 | 5/2006 | Jackson |
| 2006/0111713 A1 | 5/2006 | Jackson |
| 2006/0111730 A1 | 5/2006 | Hay |
| 2006/0149236 A1 | 7/2006 | Barry |
| 2006/0155277 A1 | 7/2006 | Metz-Stavenhagen |
| 2006/0166534 A1 | 7/2006 | Brumfield et al. |
| 2006/0166535 A1 | 7/2006 | Brumfield et al. |
| 2006/0173454 A1 | 8/2006 | Spitler et al. |
| 2006/0195092 A1 | 8/2006 | Barry |
| 2006/0200131 A1 | 9/2006 | Chao et al. |
| 2006/0200132 A1 | 9/2006 | Chao et al. |
| 2006/0217735 A1 | 9/2006 | MacDonald et al. |
| 2006/0229605 A1 | 10/2006 | Olsen |
| 2006/0229614 A1 | 10/2006 | Foley et al. |
| 2006/0247630 A1 | 11/2006 | Iott et al. |
| 2006/0264934 A1 | 11/2006 | Fallin |
| 2006/0271050 A1 | 11/2006 | Piza Vallespir |
| 2006/0282073 A1 | 12/2006 | Simanovsky |
| 2006/0293690 A1 | 12/2006 | Abdelgany |
| 2006/0293692 A1 | 12/2006 | Whipple et al. |
| 2007/0078460 A1 | 4/2007 | Frigg et al. |
| 2007/0093849 A1 | 4/2007 | Jones et al. |
| 2007/0129731 A1 | 6/2007 | Sicvol et al. |

(56) References Cited

U.S. PATENT DOCUMENTS

| | | |
|---|---|---|
| 2007/0162009 A1 | 7/2007 | Chao et al. |
| 2007/0162010 A1 | 7/2007 | Chao et al. |
| 2007/0167954 A1 | 7/2007 | Sicvol et al. |
| 2007/0173831 A1 | 7/2007 | Abdou |
| 2007/0185375 A1 | 8/2007 | Stad et al. |
| 2007/0191836 A1 | 8/2007 | Justis |
| 2007/0213715 A1 | 9/2007 | Bridwell et al. |
| 2007/0213716 A1 | 9/2007 | Lenke et al. |
| 2007/0213722 A1 | 9/2007 | Jones et al. |
| 2007/0231059 A1 | 10/2007 | Mullaney |
| 2007/0233079 A1 | 10/2007 | Fallin et al. |
| 2007/0233097 A1 | 10/2007 | Anderson et al. |
| 2007/0260261 A1 | 11/2007 | Runco et al. |
| 2007/0270880 A1 | 11/2007 | Lindemann et al. |
| 2008/0045956 A1 | 2/2008 | Songer et al. |
| 2008/0077134 A1 | 3/2008 | Dziedzic et al. |
| 2008/0077135 A1 | 3/2008 | Stad et al. |
| 2008/0172062 A1 | 7/2008 | Donahue et al. |
| 2008/0195159 A1 | 8/2008 | Kloss et al. |
| 2008/0243190 A1 | 10/2008 | Dziedzic et al. |
| 2008/0255574 A1 | 10/2008 | Dye |
| 2008/0288005 A1 | 11/2008 | Jackson |
| 2009/0018541 A1 | 1/2009 | Lavi |
| 2009/0030419 A1 | 1/2009 | Runco et al. |
| 2009/0030420 A1 | 1/2009 | Runco et al. |
| 2009/0054902 A1 | 2/2009 | Mickiewicz et al. |
| 2009/0062857 A1 | 3/2009 | Ramsay et al. |
| 2009/0082811 A1 | 3/2009 | Stad et al. |
| 2009/0088764 A1 | 4/2009 | Stad et al. |
| 2009/0138056 A1 | 5/2009 | Anderson et al. |
| 2009/0143828 A1 | 6/2009 | Stad et al. |
| 2009/0228051 A1 | 9/2009 | Kolb et al. |
| 2009/0228053 A1 | 9/2009 | Kolb et al. |
| 2010/0137915 A1 | 6/2010 | Anderson et al. |
| 2011/0034961 A1 | 2/2011 | Runco et al. |
| 2011/0034962 A1 | 2/2011 | Dunbar, Jr. et al. |
| 2011/0077689 A1 | 3/2011 | Mickiewicz et al. |
| 2011/0144695 A1 | 6/2011 | Rosenberg et al. |
| 2011/0282402 A1 | 11/2011 | Chao et al. |

FOREIGN PATENT DOCUMENTS

| | | |
|---|---|---|
| DE | 4238339 A1 | 5/1994 |
| DE | 29806563 U1 | 7/1998 |
| DE | 10005385 A1 | 8/2001 |
| DE | 10005386 A1 | 8/2001 |
| DE | 20207851 U1 | 11/2002 |
| EP | 0328883 A2 | 8/1989 |
| EP | 0381588 B2 | 8/1990 |
| EP | 0441729 B1 | 8/1991 |
| EP | 0487895 A1 | 6/1992 |
| EP | 0572790 B1 | 12/1993 |
| EP | 0592266 A1 | 4/1994 |
| EP | 0669109 B1 | 8/1995 |
| EP | 0558883 B1 | 7/1997 |
| EP | 0784693 A1 | 7/1997 |
| EP | 0880344 B1 | 12/1998 |
| EP | 0885598 A2 | 12/1998 |
| EP | 0948939 A1 | 10/1999 |
| EP | 0951246 B1 | 10/1999 |
| EP | 1023873 A2 | 8/2000 |
| EP | 1090595 A2 | 4/2001 |
| EP | 1295566 A1 | 3/2003 |
| EP | 1364622 B1 | 11/2003 |
| EP | 1574175 A1 | 9/2005 |
| FR | 2677242 A1 | 12/1992 |
| FR | 2680314 A1 | 2/1993 |
| FR | 2729291 A1 | 7/1996 |
| JP | 2003-52708 | 2/2003 |
| JP | 2007-525274 | 9/2007 |
| WO | 90/02527 A1 | 3/1990 |
| WO | 96/21396 A1 | 7/1996 |
| WO | 98/22033 A1 | 5/1998 |
| WO | 98/25534 A1 | 6/1998 |
| WO | 99/44527 A1 | 9/1999 |
| WO | 01/45576 A1 | 6/2001 |
| WO | 02/07622 A1 | 1/2002 |
| WO | 02/102259 A2 | 12/2002 |
| WO | 03/007828 A1 | 1/2003 |
| WO | 03/032863 A2 | 4/2003 |
| WO | 03/049629 A1 | 6/2003 |
| WO | 2004/019755 A2 | 3/2004 |
| WO | 2004/034916 A1 | 4/2004 |
| WO | 2005/006948 A2 | 1/2005 |
| WO | 2005/013839 A2 | 2/2005 |
| WO | 2005/030065 A1 | 4/2005 |
| WO | 2005/044117 A2 | 5/2005 |
| WO | 2005/044123 A1 | 5/2005 |
| WO | 2005/072081 A2 | 8/2005 |
| WO | 2006/020443 A1 | 2/2006 |
| WO | 2007/092797 A2 | 8/2007 |
| WO | 2007/092870 A2 | 8/2007 |
| WO | 2007/092876 A2 | 8/2007 |
| WO | 2007/149426 A2 | 12/2007 |
| WO | 2008/024937 A2 | 2/2008 |

OTHER PUBLICATIONS

International Preliminary Report on Patentability for Application No. PCT/US2009/036343, dated Sep. 14, 2010.
Canadian Office Action for Application No. 2,717,758, 2 pages, dated May 4, 2012.
Chinese Office Action for Application No. 200980116856.2, 10 pages, dated Apr. 18, 2012.
Wiltse, Leon L. et al., "History of Pedicle Screw Fixation of the Spine," Spine, State of the Art Reviews, vol. 6(1):1-10 (1992).
European Office Action for Application No. 06736870, dated Dec. 18, 2009.
European Office Action for Application No. 06735464.7, dated Apr. 14, 2010.
International Search Report for Application No. PCT/US06/05811, dated Sep. 13, 2007.
International Search Report and Written Opinion for Application No. PCT/US06/40621, dated May 18, 2007.
Sofamor, The Spine Specialist, "Introducteur-Centreur De Tige," 7 pages (1994).
International Search Report and Written Opinion for Application No. PCT/US06/40621, 6 pages, dated May 18, 2007.
International Search Report for Application No. PCT/US2008/068515, 3 pages, dated Jan. 2, 2009.
Supplementary European Search Report for Application No. 09719006.0, 8 pages, dated Mar. 6, 2013.
Japanese Office Action for Application No. 2010-550787, 7 pages, dated May 7, 2013.
Japanese Office Action for Application No. 2010-550787, 4 pages, dated Sep. 17, 2013.

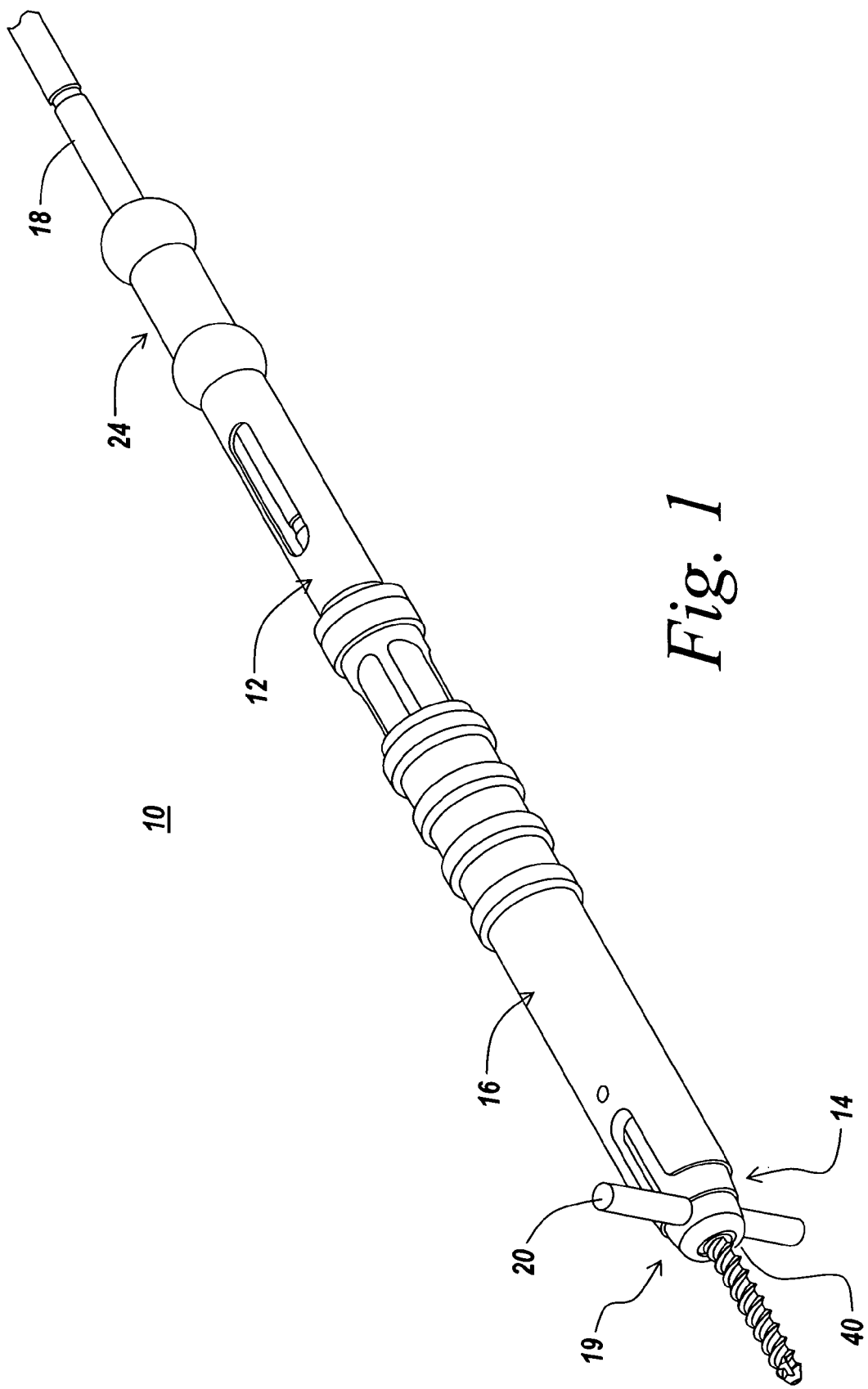

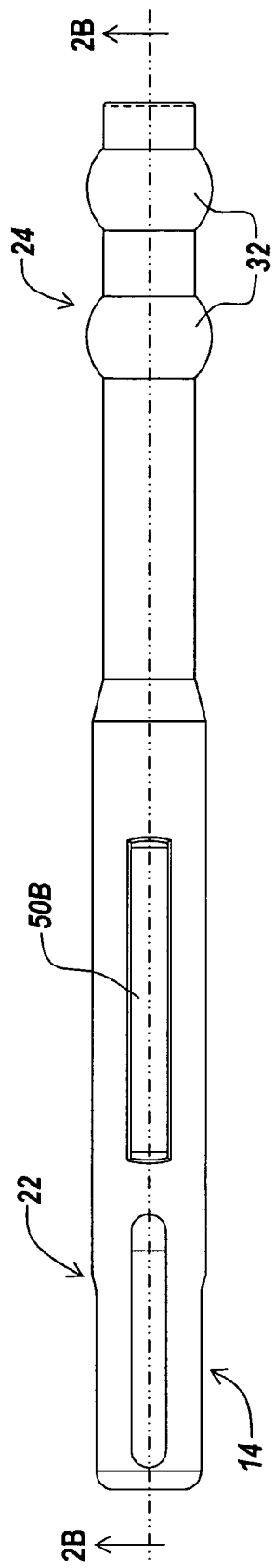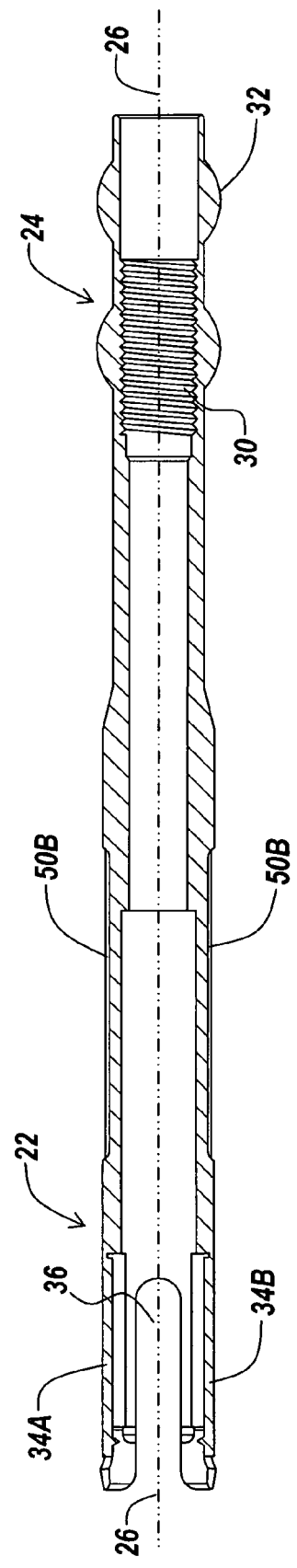
Fig. 2A
Fig. 2B

DEROTATION INSTRUMENT WITH REDUCTION FUNCTIONALITY

BACKGROUND

In spinal deformity surgical procedures, the curvature of the spine (e.g., the coronal curvature of the spine and/or the sagittal curvature of the spine) can be corrected by the implantation of a construct of bone anchors and spinal fixation elements. Examples of bone anchors used in such a construct include hooks and bone screws. An examples of spinal fixation elements used in such a construct is a rod During one type of spinal surgery, a surgeon first exposes the posterior spine and attaches bone anchors to selected vertebrae of the spine. The surgeon then inserts a spinal fixation element into receiving portions of the bone anchors to connect the selected vertebrae, thereby fixing the relative positions of the vertebrae.

Generally, a controlled mechanical force is required to bring together the spinal fixation element and a bone anchor in a convenient manner. This procedure is typically referred to as "reduction." To complete a reduction, a surgeon must insert a locking mechanism, such as a set screw, into the vertebral anchor to lock the spinal rod to the implant before the force for inserting the rod can be removed.

In addition to correcting the curvature of the spine, the angular rotation of one or more vertebrae relative to other vertebrae may also be corrected. Conventional surgical procedures for correcting the angular rotation of a vertebra involve rotating the spinal fixation element, for example, a spinal rod, connected to the vertebra by a bone anchor. In the case of constructs that include a spinal rod, this procedure is typically referred to as "vertebral body derotation." Vertebral body derotation can place significant stress on the interface between the bone anchors connected to the rotated spinal rod and the vertebra in which each bone anchor is implanted. This stress can cause a failure of one or more of the bone anchors or harm to the vertebra. Accordingly, there is a need for improved instruments and methods for manipulating a vertebra.

Conventional derotation instruments are designed to be used after reduction has been performed and the spinal fixation element has been secured to the bone anchor. However, the bone anchors often bind on the fixation element during the rotation, preventing the motion or requiring significant force to obtain it. Thus, in some instances it may be beneficial to perform derotation before reduction. In addition, reduction and derotation require different instruments. Thus, one instrument must be removed to allow the other to be used.

SUMMARY

Disclosed herein are instruments and methods for manipulating a bone anchor and a spinal fixation element. The instruments and methods disclosed herein are particularly suited to facilitate rotation of a bone anchor relative to another bone to correct the angular rotation of the vertebrae attached to the bone anchor. The instrument does not require the spinal fixation element to be inserted into the bone anchor prior to manipulation. The instrument further may be used in the insertion of the spinal fixation element into the bone anchor in a reduction.

In accordance with one example embodiment, an instrument for manipulating a vertebra may comprise a shaft having a proximal end, a distal end and a lumen extending between the proximal end and the distal end; one or more fingers disposed at the distal end of the shaft defining a slot, an outer sleeve disposed about the shaft and configured to slide over the distal end of the shaft, and a reduction element. The outer sleeve slides between a first position and a second position. When the outer sleeve is in the first position, the one or more fingers are unconstrained by the outer sleeve allowing the one or more fingers to receive the spinal fixation element in the slot and engage the spinal fixation element receiving member. When the outer sleeve is in the second position, the one or more fingers are constrained by the outer sleeve securing the spinal fixation element in the slot and the engagement of the spinal fixation element receiving member of the bone anchor by the one or more fingers to permit manipulation of the spinal fixation element and bone anchor by the instrument. The reduction element is configured to pass through the lumen of the shaft and engage the offset spinal fixation element to reduce the offset spinal fixation element into the spinal fixation element receiving member of the bone anchor.

In accordance with another example embodiment, a system for manipulating one or more vertebra may comprise a first instrument as described above, a second instrument as described above, and a connector connecting the first instrument and the second instrument. The connector, in the example embodiment, may include a first receiving element for receiving the first instrument and a second receiving element for receiving the second instrument. The first receiving element may be adjustable relative to the second receiving element.

In accordance with another example embodiment, a method of manipulating a bone anchor and spinal fixation element comprises connecting a bone anchor to a vertebra, positioning a spinal fixation element in proximity to a receiving member of the bone anchor; connecting an instrument as described above; and manipulating the first instrument to rotate first bone anchor and the spinal fixation element. The spinal fixation element may also be reduced into the bone anchor using the reduction element.

BRIEF DESCRIPTION OF THE FIGURES

These and other features and advantages of the instruments and methods disclosed herein will be more fully understood by reference to the following detailed description in conjunction with the attached drawings in which like reference numerals refer to like elements through the different views. The drawings illustrate principles of the instruments and methods disclosed herein and, although not to scale, show relative dimensions.

FIG. 1 is a perspective view of an example embodiment of an instrument for manipulating a vertebral body, illustrating the instrument engaging a bone anchor;

FIG. 2A is a top elevation view of the shaft of the instrument of FIG. 1, illustrating the shaft separate from the other elements of the instrument;

FIG. 2B is a side elevational view in cross section of shaft the instrument of FIG. 1, illustrating the shaft separate from the other elements of the instrument;

DETAILED DESCRIPTION OF THE INVENTION

Figure 3:
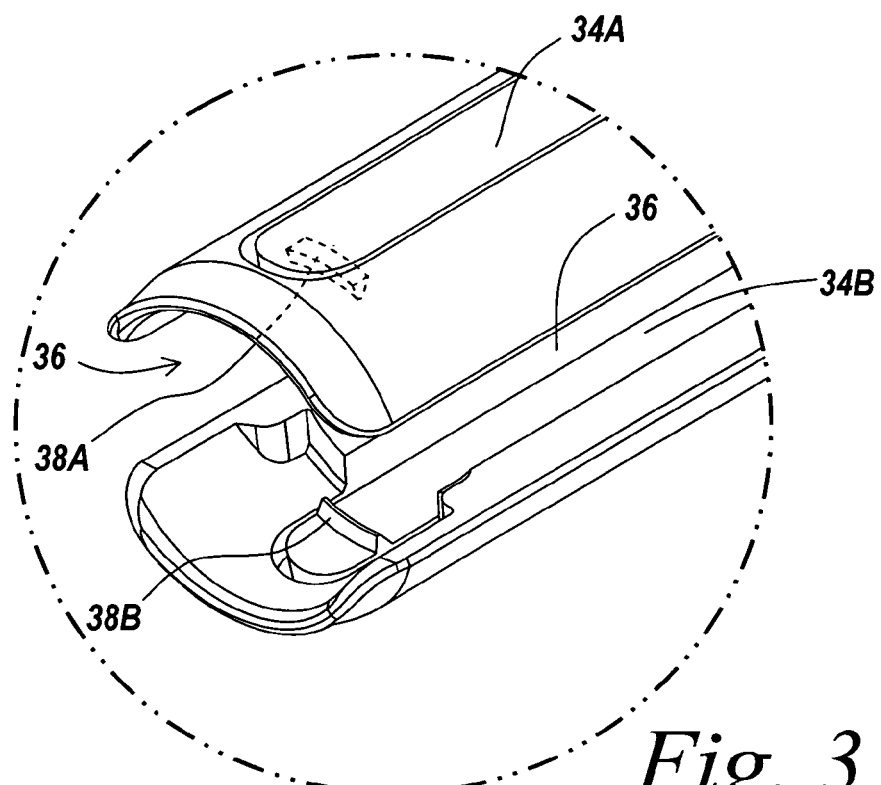
FIG. 3 is a perspective view of the engagement mechanism of the instrument of FIG. 1, illustrating the engagement mechanism separate from the other elements of the instrument.

Certain example embodiments will now be described to provide an overall understanding of the principles of the structure, function, manufacture, and use of the instruments and methods disclosed herein. One or more examples of these embodiments are illustrated in the accompanying drawings. Those of ordinary skill in the art will understand that the instruments and methods specifically described herein and illustrated in the accompanying drawings are non-limiting example embodiments and that the scope of the present invention is defined solely by the claims. The features illustrated or described in connection with one example embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIG. 1 illustrates an example embodiment of an instrument for manipulating a bone anchor and, in turn, a vertebral body to which the bone anchor is attached. The example instrument 10 includes a shaft 12, an anchor engagement mechanism 14, an outer sleeve 16 disposed about the shaft 12, and a reduction element 18. The example instrument 10 may be employed to manipulate a bone anchor 1919 and spinal fixation element 20 for implantation or adjustment. The example instrument 10 may also be used to engage a bone anchor 19 implanted in a vertebra and maneuver the bone anchor 19 and the vertebra by manipulating the instrument 10. For example, the example instrument 10 may be employed to rotate the bone anchor 19, and the vertebra relative to other vertebrae and thereby by correct the angular orientation of the vertebra. The instrument 10, when employed in the example manner, thus may be used to effect segmental correction of the angular orientation of the vertebrae of the spine as well as reduce the spinal fixation element 20 into the bone anchor 19 using the reduction element 18.

The example instrument 10 may be constructed of any biocompatible material including, for example, metals, such as stainless steel or titanium, polymers, ceramics, or composites thereof. The length and diameter of the instrument 10 may vary depending on the area of the spine being treated (e.g., lumbar, thoracic, or cervical) and the approach (e.g., posterior, anterior, or lateral). For example, the length of the instrument 10 may be selected to at least span from a skin incision to proximate a vertebra. The diameter of the instrument 10 may be selected to facilitate positioning of the instrument 10 through an open incision or a minimally invasive incision. In certain example embodiments, for example, the diameter of the instrument may be selected to facilitate delivery of the instrument 10 through a minimally invasive access device such as a cannula or expandable retractor.

For purposes of illustration, each of the elements of the example instrument 10 will be discussed independently and in conjunction with the other elements.

FIGS. 2A and 2B illustrate the shaft 12 separate from the rest of the example instrument 10. The shaft 12 of the example instrument 10 may have a distal end 22, a proximal end 24, and a lumen 26 extending between the proximal end 24 and the distal end 22. In the example embodiment, the shaft 12 is generally tubular in shape having an approximately circular cross section. One skilled in the art will appreciate that the shaft 12 may have other cross sectional shapes including elliptical or rectilinear. The lumen 26 of the shaft 12 is sized to receive reduction element 18, reduction element. In other embodiments, the reduction element 18, or a portion of the reduction element may be removed and other instruments, such as a screwdriver or the like, may be passed through the shaft 12.

In certain embodiments, the shaft 12 may further include surface configurations configured to mate with the reduction element 18 to assist in the interoperation of the shaft with the reduction element 18. For example, the lumen 26 of the shaft 12 may include threads 30 for directing the insertion of the reduction element 18 thru the lumen 26. The proximal end 24 of the shaft may also have connection elements 32 for connecting the instrument 10 to a connecter. The connector may be used to connect multiple instruments. The interoperation of the shaft with other elements will be discussed in more detail below.

At the distal end 22 of the shaft 12 is the engagement mechanism 14. The engagement mechanism 14 is configured to engage a bone anchor 19, such as, for example, a hook, a monoaxial bone screw, or a polyaxial bone screw, and thereby connect the instrument 10 to the bone anchor 19 in a manner sufficient to permit manipulation of the bone anchor and the vertebra in which the bone anchor is implanted. The engagement mechanism 14 also serves to capture a spinal fixation element 20 such as a spinal rod that may or may not be inserted into the bone anchor 19. In the example embodiment, the anchor engagement mechanism 14 is one or more fingers 34A and 34B at the distal end 22 of the shaft 12 which define a slot 36 disposed between the fingers 34A and 34B

A magnified depiction of fingers 34A and 34B can be seen in FIG. 3. In certain example embodiments, fingers 34A and 34B may be flexible and resilient in the radial direction to facilitate connection to a bone anchor. For example, the fingers 34A and 34B may be flexed apart in the radial direction from a first, relaxed position to facilitate advancement of the fingers longitudinally over a portion of the bone anchor 19. Once positioned about a portion of the bone anchor 19, the fingers 34A and 34B may provide a radially compressive force on the bone anchor as the fingers 34A and 34B attempt to return to the first, relaxed position.

In the illustrated example embodiment, each finger 34A and 34B may include one or more radially inward facing projections 38A, 38B that are sized and shaped to seat within an opening provided in a portion of the bone anchor 19 to facilitate retention of the bone anchor 19 by the fingers 34A and 34B. The size, shape and number of projections can be varied depending on, for example, the opening(s) provided on the bone anchor and type of connection desired. Further examples of how the anchor engagement mechanism 14 interacts with a bone anchor 19 will be discussed below.

The slot 36 separates fingers 34A and 34B. The slot 36 is configured to receive a spinal fixation element 20 that may be offset from the bone anchor 19. The example instrument 10 allows for the manipulation of the bone anchor 19 without requiring the spinal fixation element 20 to be inserted into the bone anchor 19. The slot 36 may be of significant size to allow the spinal fixation element 20 to be offset from spinal fixation element receiving member 40 of the bone anchor 19 while still allowing the fingers 34A and 34B to engage and retain the bone anchor 19. In certain embodiments, the slot 36 may extend approximately 20 mm from the distal end 22 of the shaft 12.

In certain embodiments, the engagement mechanism 14 may further serve to capture or otherwise retain the spinal fixation element 20 in proximity to the bone anchor 19 while the bone anchor is manipulated. The fingers 34A and 34B may also be used to guide the spinal fixation element 20 into the receiving member 40 of the bone anchor 19 during reduction.

While the example embodiment of the engagement mechanism 14 discussed herein has featured two fingers 34A and 34B, it should be understood that the present invention may also be implemented with only one finger or other finger configurations without departing from the scope or spirit of the invention. Other implementations and configuration will be apparent to one skilled in the art given the benefit of this disclosure.

Figure 4A:
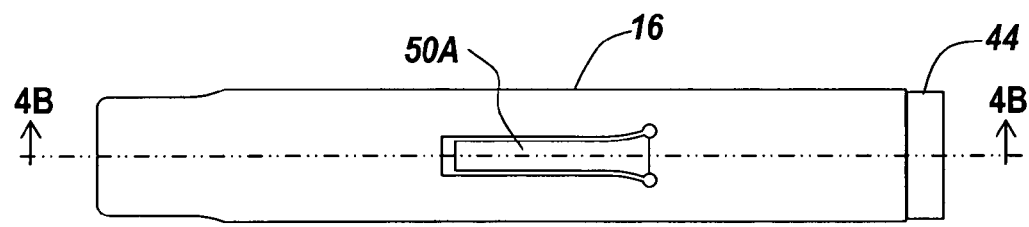
FIG. 4A is a top elevation view of the sleeve of the instrument of FIG. 1, illustrating the sleeve separate from the other elements of the instrument.
Figure 4B:
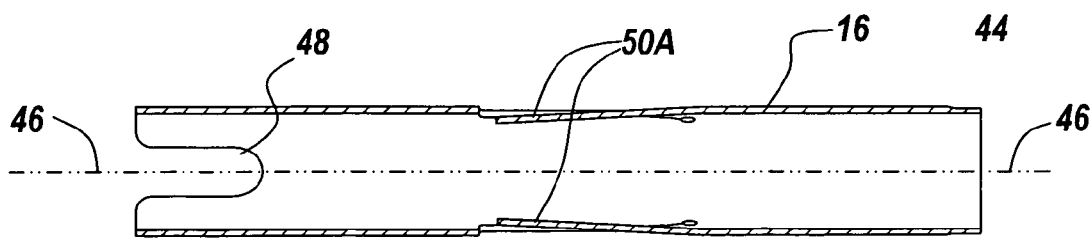
FIG. 4B is a side elevational view in cross section of sleeve the instrument of FIG. 1, illustrating the sleeve separate from the other elements of the instrument.

FIGS. 4A and 4B illustrates the outer sleeve 16 separate from the rest of the example instrument 10. The outer sleeve 16 of the example instrument 10 is disposed about the shaft 12 and may have a distal end 42, a proximal end 44, and a lumen 46 extending between the proximal end 44 and the distal end 42. The outer sleeve 16 and the shaft 12 may have complementary shapes to facilitate positioning of the outer sleeve 16 over the inner shaft 12. For example, in the illustrated embodiment, the outer sleeve is generally tubular in shape. The longitudinal axis of the outer sleeve 16 is coincident with the longitudinal axis of the elongate shaft 12. The shaft 12 may be disposed within the lumen 46 of the outer sleeve 16 allowing the outer sleeve 16 to be movable relative to the shaft 12. For example, the outer sleeve 16 may be movable along the longitudinal axis of the shaft 12. In certain embodiments, the sleeve 16 and shaft 12 may have interlocking surface configuration 50A and 50B that maintain the orientation of the sleeve 16 on the shaft 12 as the sleeve 16 is moved along the shaft 12. For example, the surface configuration 50A on the sleeve 16 may be a tab and the surface configuration 50B may be a groove that receives the tab. In other embodiments, the sleeve 16 may include a locking feature that allows a user to lock the sleeve 16 in position along the shaft 12.

In the example embodiment, the sleeve 16 further includes a slot 48 corresponding to the slot 36 of the engagement mechanism 14. The slot 48, like the slot 36, is configured to receive a spinal fixation element 20 (See FIG. 1) that may be offset from the receiving member 40 of the bone anchor 19 that allows the bone anchor 19 to be engaged without requiring the spinal fixation element 20 to be inserted in the receiving member 40 of the bone anchor 19.

Figure 5A:
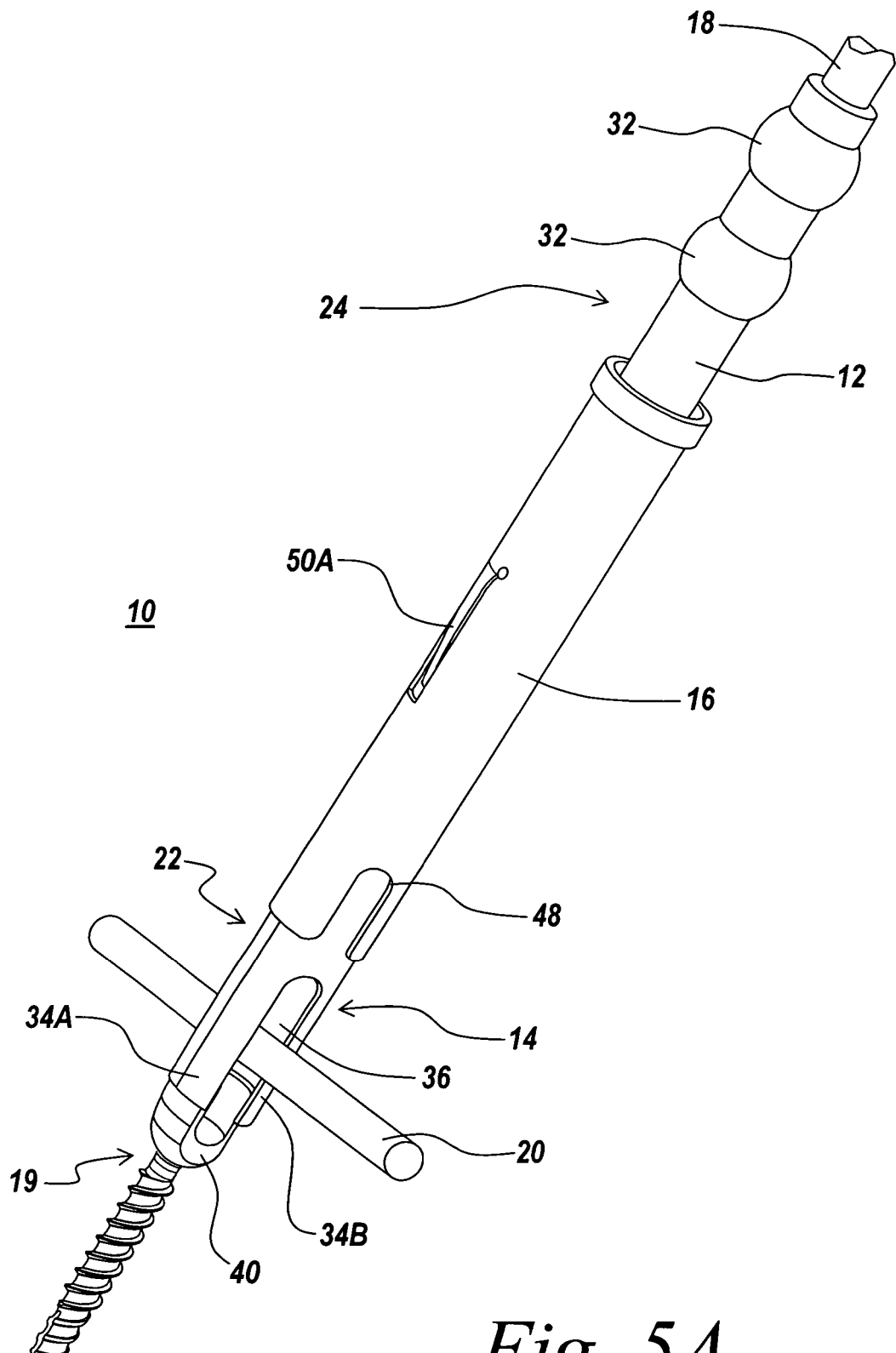
FIG. 5A is a perspective view of the instrument of FIG. 1, illustrating the sleeve in a first position.

The outer sleeve 16 is slidable along the distal end 22 of the shaft 12 to interact with the engagement mechanism 14. Examples of this can be seen in FIGS. 5A and 5B. The outer sleeve 16 may be movable relative to the shaft 12 between a first, proximal position in which the fingers 34A and 34B of the engagement mechanism 14 are unconstrained and advanced beyond a distal end 42 of the outer sleeve 16, and a second, proximal position in which a substantial portion of the fingers 34A and 34B are disposed within and constrained by the sleeve 16. The fingers 34A and 34B, when the sleeve 16 is in the first position, may be configured to encapsulate and capture the bone anchor 19 and spinal fixation element 20 therebetween as seen In FIG. 5A. In the example embodiment, for example, fingers 34A and 34B may move apart from one another when the sleeve 16 is moved to the first position to facilitate positioning of the receiving member 40 of the bone anchor 19, between the fingers 34A and 34B.

Figure 5B:
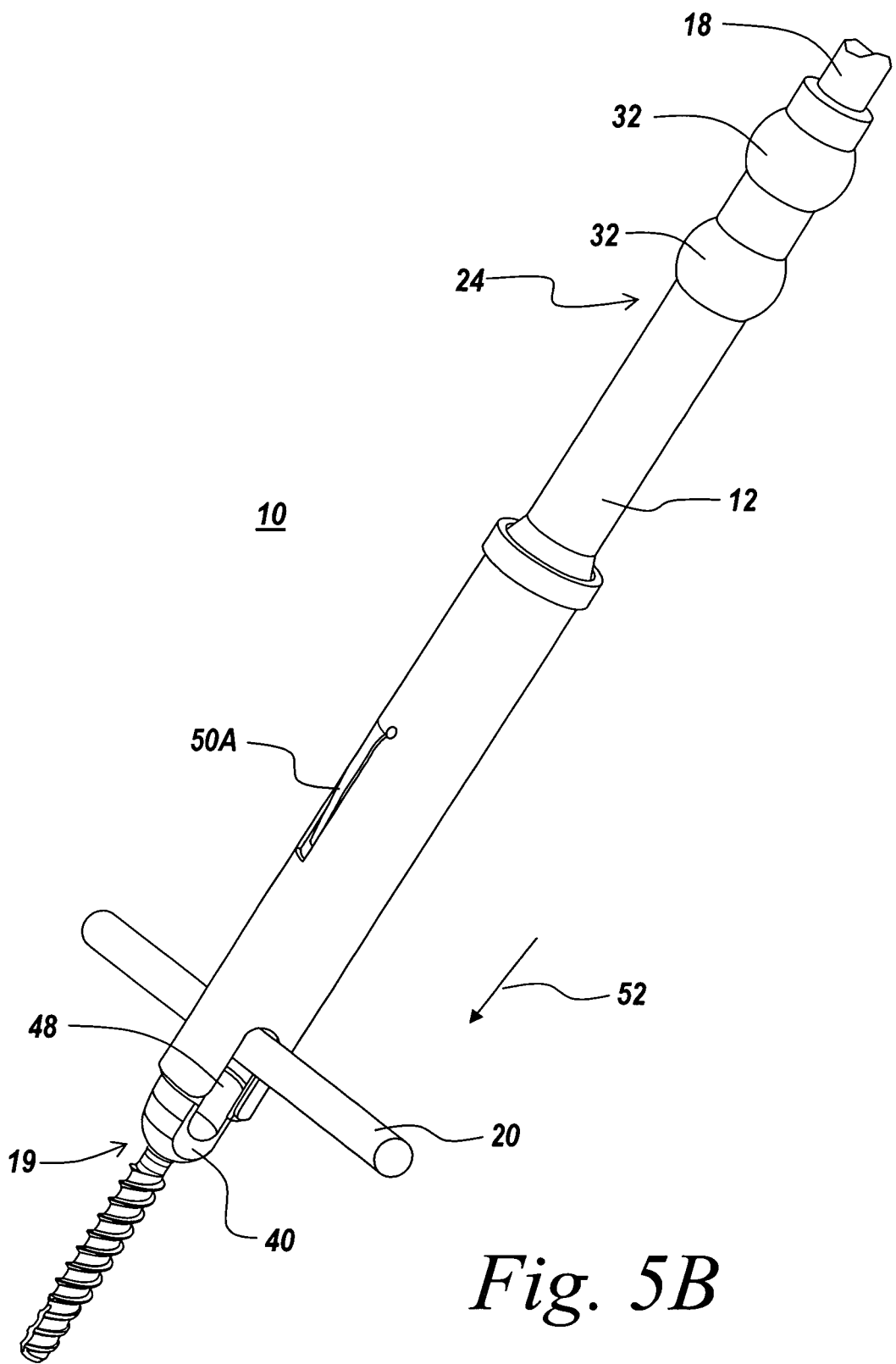
FIG. 5B is a perspective view of the instrument of FIG. 1, illustrating the sleeve in a second position.

When the sleeve 16 is moved in the direction of arrow 52 to the second, distal position, fingers 34A and 34B may maintain capture of the bone anchor 19 to further retain the bone anchor 19 and spinal fixation element 20 between the fingers 34A and 34B as seen in FIG. 5B. The fingers 34A and 34B may be constrained and inhibited from separating by the outer sleeve 16 when in the second, distal position. As such, the interaction of the sleeve 16 and the engagement mechanism 14 act as a collet to retain the bone anchor 19. In the example embodiment, for example, the bone anchor 19 is retained between the fingers 34A and 34B in a manner sufficient to permit maneuvering of the spinal fixation device 20, bone anchor 19, and a vertebra in which the bone anchor 19 is implanted by manipulation of the instrument. For example, the spinal fixation device 20, bone anchor 19, and vertebra may be manipulated, moved along the axis of the instrument 10, and/or moved in a direction perpendicular to the axis to the instrument 10 by the instrument 10.

Figure 5C:
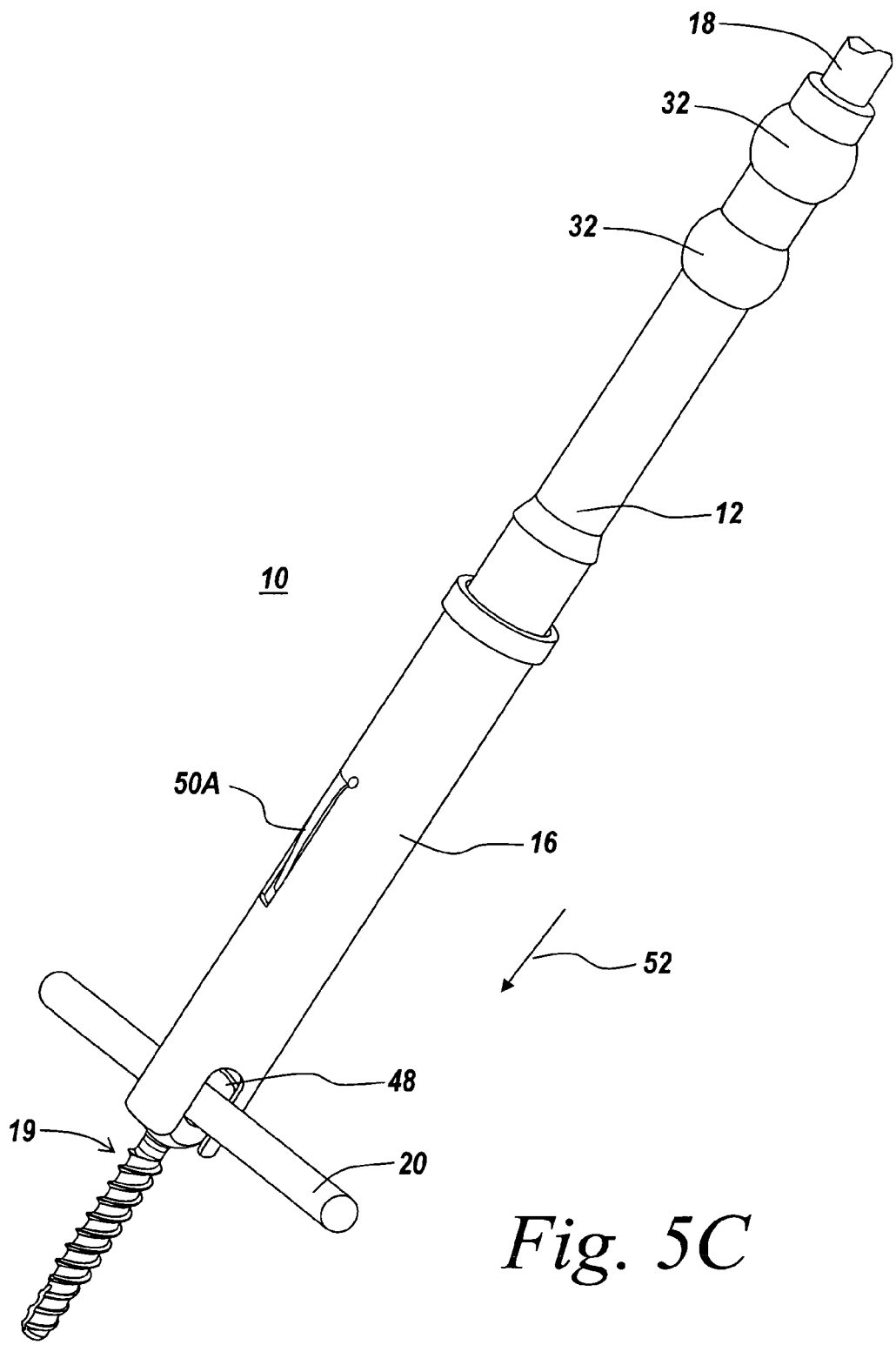
FIG. 5C is a perspective view of the instrument of FIG. 1, illustrating the sleeve in a third position.

In certain embodiments, the sleeve 16 may be further moved to a third distal position as seen In FIG. 5C. When the sleeve 16 is moved to the third position, the sleeve 16 may engage the spinal fixation element 20 received in slot 48 and serve to push the spinal fixation element 20 into the receiving member 40 of the bone anchor 19. Thus, the sleeve 16 may be used in the reduction, or partial reduction of the spinal fixation element 20.

While the sleeve 16 has been described as uniform piece, it should be understood that the sleeve 16 may be made of multiple parts without departing from the spirit and scope of the invention. For example, the sleeve 16 may have one part used to constrain the fingers 34A and 34B and another part used to reduce the spinal fixation element 20. Other implementations and configuration will be apparent to one skilled in the art given the benefit of this disclosure.

Figure 6A:
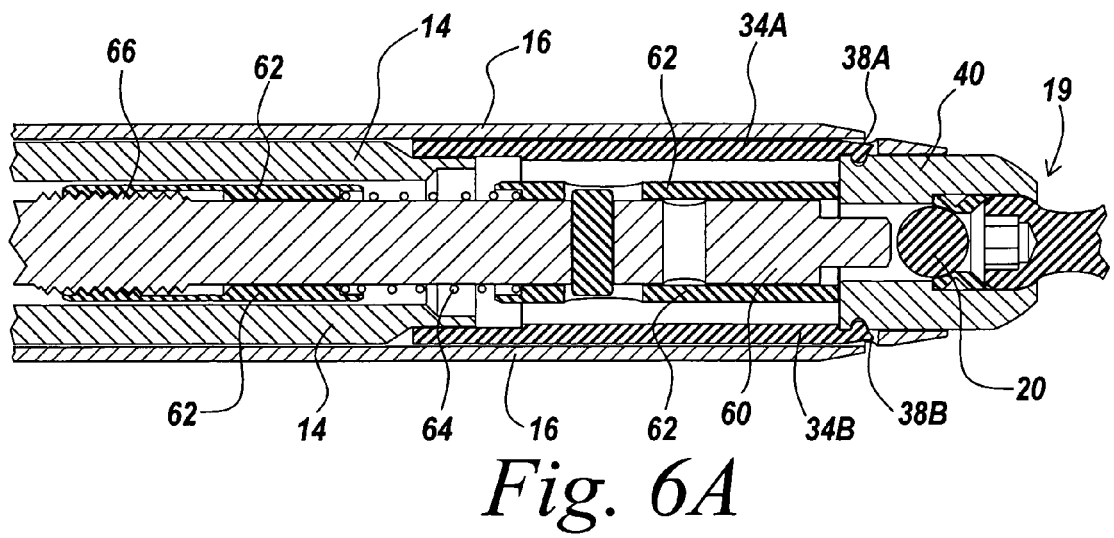
FIG. 6A is a side elevational view in cross section of the distal end of the instrument of FIGS. 1-5B showing the interaction of the instrument with a bone anchor and an insertion instrument.

In some embodiments, the reduction element 18 is used to effect reduction of the spinal fixation element 20 into the receiving member 40 of the bone anchor 19. FIG. 6A depicts a cross sectional view of the distal end of the example instrument 10 which the reduction element 18 being used for reduction of the spinal fixation element 20. In this example, the finger 34A and 34B of the engagement mechanism 14 have engaged and captured the bone anchor 19. Protrusions 38A and 38B have engaged receiving member 40 of the bone anchor 19. The sleeve 18 has also been moved to the second distal position constraining fingers 34A and 34B to secure the bone anchor 19. The reduction element 18 passes through the lumen 26 of the shaft 12 such that the distal end 60 of the instrument 18 engages and pushes the spinal fixation element 20 into the receiving member 40 of the bone anchor 19. In certain embodiment the reduction element 18 may have threads configured to engage threads 30 in the lumen 26 of the shaft 12 (See FIG. 2B). Thus, by rotating the reduction element 18, the threads 30 serve to advance the reduction element 18 to effect reduction.

The reduction element 18 may also be provided with a centering mechanism 62 that makes sure the reduction element 18 is centered in the lumen 26 of the shaft 12. In the example of FIG. 6A, the centering mechanism 62 is a housing. In this example, the housing 62 also includes a spring biasing mechanism 64 that engages a set of threads 66 when the distal end 60 of the instrument meets the spinal fixation element 20.

Figure 6B:
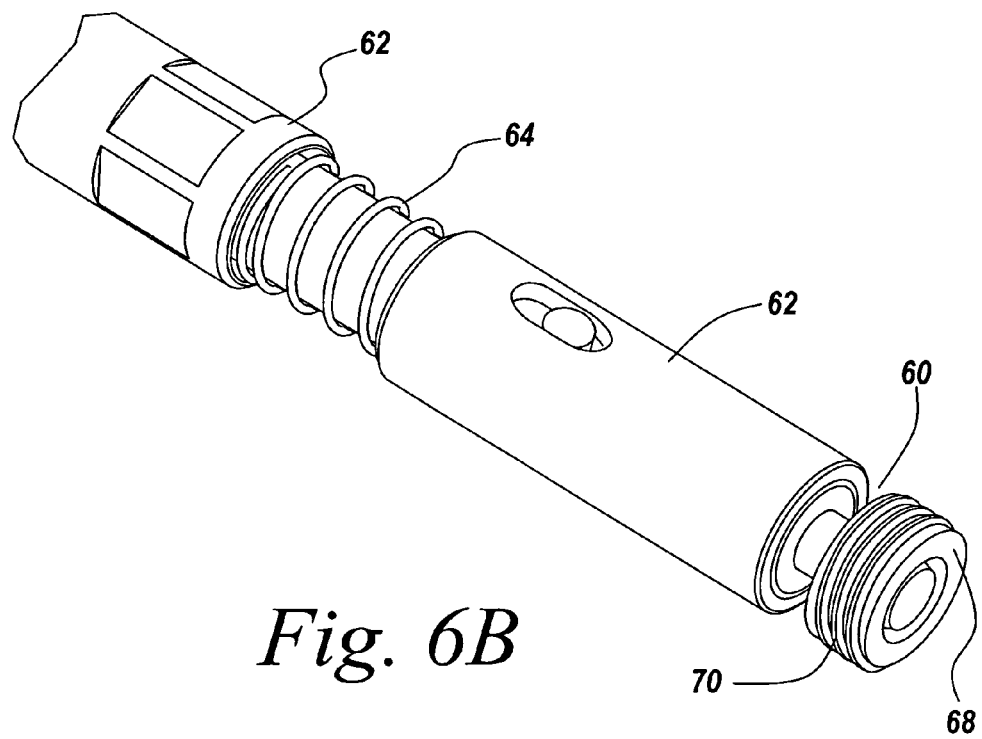
FIG. 6B is a perspective view of the distal end of an installation instrument of FIG. 6A showing the interaction of the instrument with locking mechanism.

In certain embodiments, the reduction element 18 may also be used to insert a locking element 68, such as a set screw, to secure the spinal fixation element 20 after reduction. An example of this can be seen in FIG. 6B. Here the set screw 69 is place on the distal end 60 of the reduction element 18, which serves to reduce the spinal fixation element 20 as well at insert the set screw 68. The spring biasing mechanism 64 may provide some play between the threads 70 of the set screw 68 and the threads of the reduction element 18 in instances where the threading of the reduction element 18 and the threading of the set screw 68 are not synchronized with the threading of the receiving member 40.

In other embodiments, the reduction element 18 may include multiple parts. For example, one part may be used for reduction, while another part is used for inserting the set screw 68. An example of this can be seen in FIGS. 7A and 7B.

Figure 7A:
FIG. 7A is a side elevational view in of the instrument of FIGS. 1-5B showing the interaction of the instrument with a bone anchor and an insertion instrument.
Figure 7B:
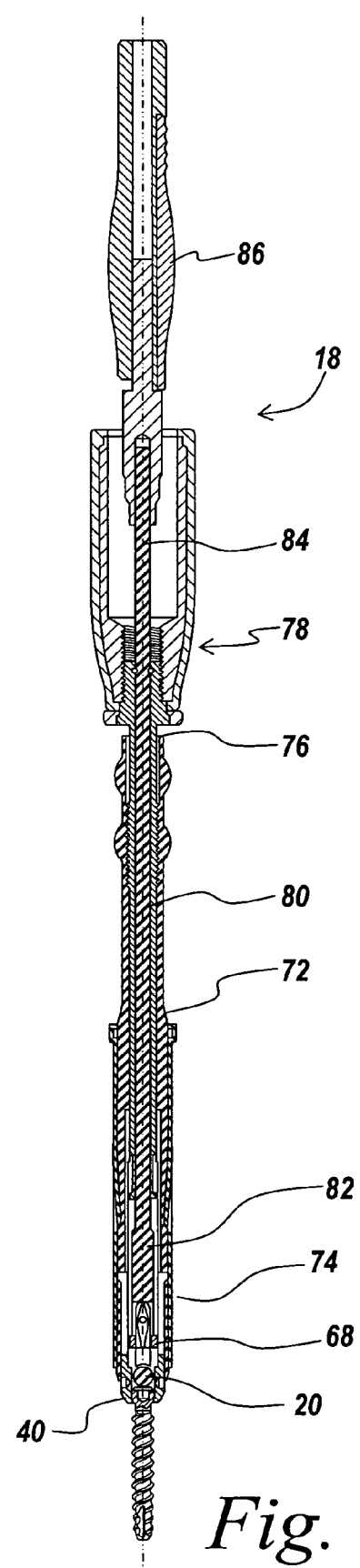
FIG. 7B is a side elevational view in cross section of the instrument of FIGS. 1-5B showing the interaction of the instrument with a bone anchor and an insertion instrument.

FIG. 7A is a side view of one embodiment of a reduction instrument 18 having two separate portions. FIG. 7B is a cross sectional view of the reduction element 18 in FIG. 7A. In this embodiment, the reduction element 18 includes a first portion for reduction and a second portion for inserting the set screw 68. The first portion includes a shaft 72 having a distal end 74, a proximal end 76, and lumen extending from the proximal end 76 to the distal end 74. The first portion further includes a handle 78 as the proximal end 76 of the shaft 72. The second portion also includes a shaft 80 having a distal end 82 and a proximal end 84. The shaft 80 of the second portion passes through the lumen of the shaft 72 of the first portion. The second portion also includes a handle 86 at the proximal end 84 of the shaft 80. Because the shaft 80 of the second portion passes through the shaft 72 of the first portion, each portion of the reduction element 18 can be operated independently of the other portion. Thus, to effect reduction, a user may use the handle 78 of the first portion to advance shaft 72 through the lumen 26 of the shaft 12 of the example instrument 10 to engage the spinal fixation element 20. Likewise, to insert the set screw 68, the user may use handle 86 to advance the shaft 80 of the second portion to insert a set screw 68 on the distal end 82 of shaft 80 into the receiving portion 40 of the bone anchor 19.

The ability to capture and retain a bone anchor 19 by the instrument 10 provides the ability to manipulate bone anchor 19 for adjustment. Accordingly, another example use of the instrument 10 is for de-rotation.

As previously discussed, the example instrument 10 may include a connection element 32 configured to engage a connector, such as the example connector 100 described below, for connecting the instrument 10 to another instrument, for example, another instrument for manipulating a vertebra. In the illustrated example embodiment, for example the shaft 14 includes a connection element 32 positioned at the proximal end 24 of the shaft 14. The connection element 32 may be configured to permit polyaxial motion of the instrument 10 relative to the connector. For example, the connection element 32 of the example embodiment may be at least partially spherical in shape to engage a complementary shaped receiving element of the connector. Other possible geometries and configurations will be apparent to one skilled in the art given the benefit of this disclosure.

FIGS. 8-11 illustrate one example embodiment of a connector 100 for connecting two or more instruments and facilitating cooperative movement of the instruments. The example connector 100 is particularly suited to connecting one or more instruments for manipulating a vertebra, such as the instrument 10 described above. One skilled in the art will appreciate; however, the connector 100 may be used to connect any type of spinal or surgical instruments.

It should also be understood that the example connector 100 is but one possible example of any number of possible configurations. Other possible embodiments, implementations, and configurations of connectors, receiving elements, and latch mechanisms will be apparent to one skilled in the art given the benefit of this disclosure.

The example connector 100 may include a plurality of receiving elements 102A and 102B, each of which connects to an instrument. Any number of the receiving elements 102A and 102B may be provided. In the illustrated example embodiment, the connector 100 includes a first adjustable receiving element 102A for receiving a first instrument and a second receiving element 102B for receiving a second instrument. The first receiving element 102A and/or the second receiving element 102B may be adjustable relative to one another to facilitate connection to two spaced apart instruments. For example, in the illustrated example embodiment, the first receiving element 102A is adjustable relative to the second receiving element 102B and the connector 100 and the second receiving element 102B is fixed relative to the connector 100.

Figure 8:
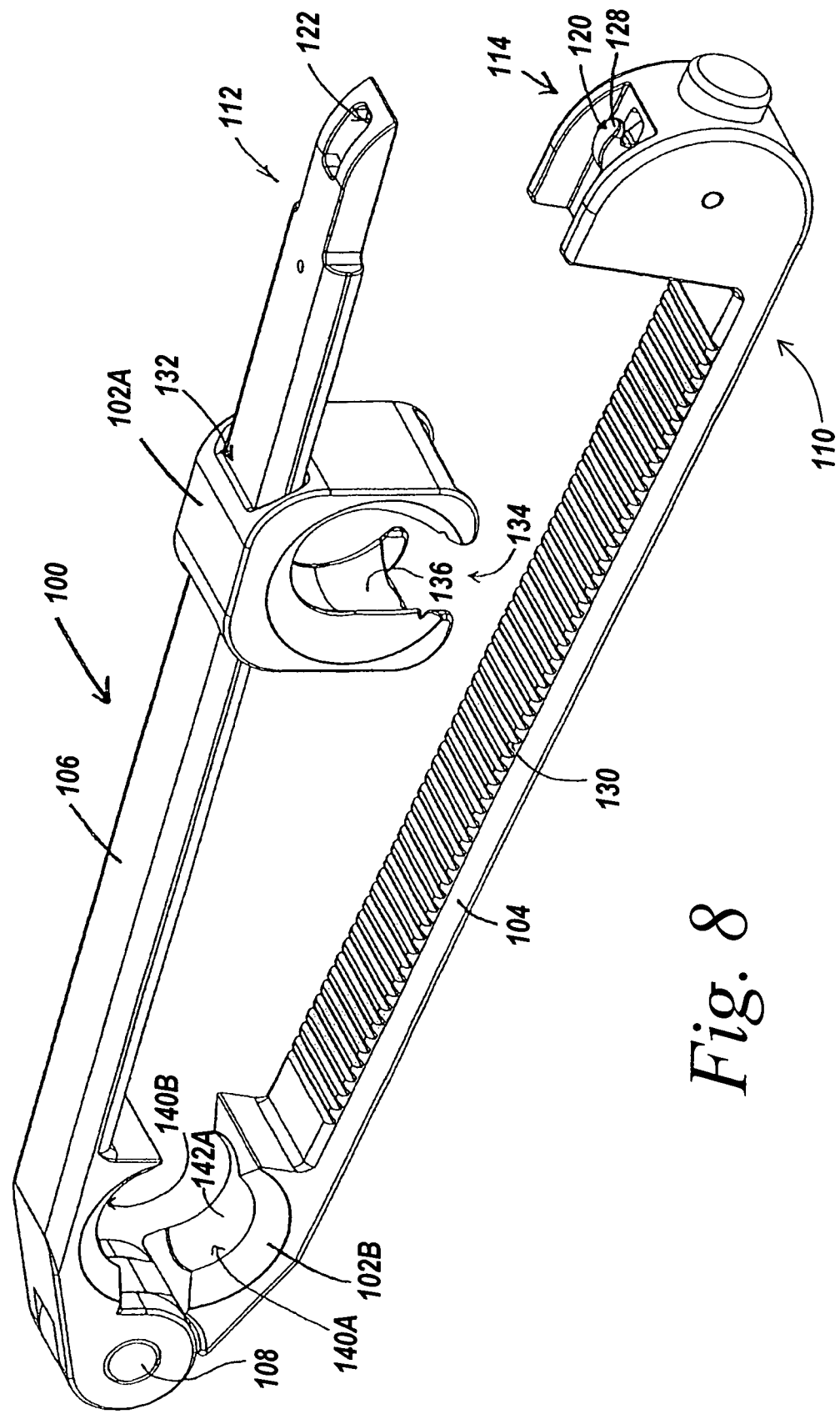
FIG. 8 is a perspective view of a connector for connecting two instruments, such as the instrument of FIG. 1, illustrating the connector in an open position.
Figure 9:
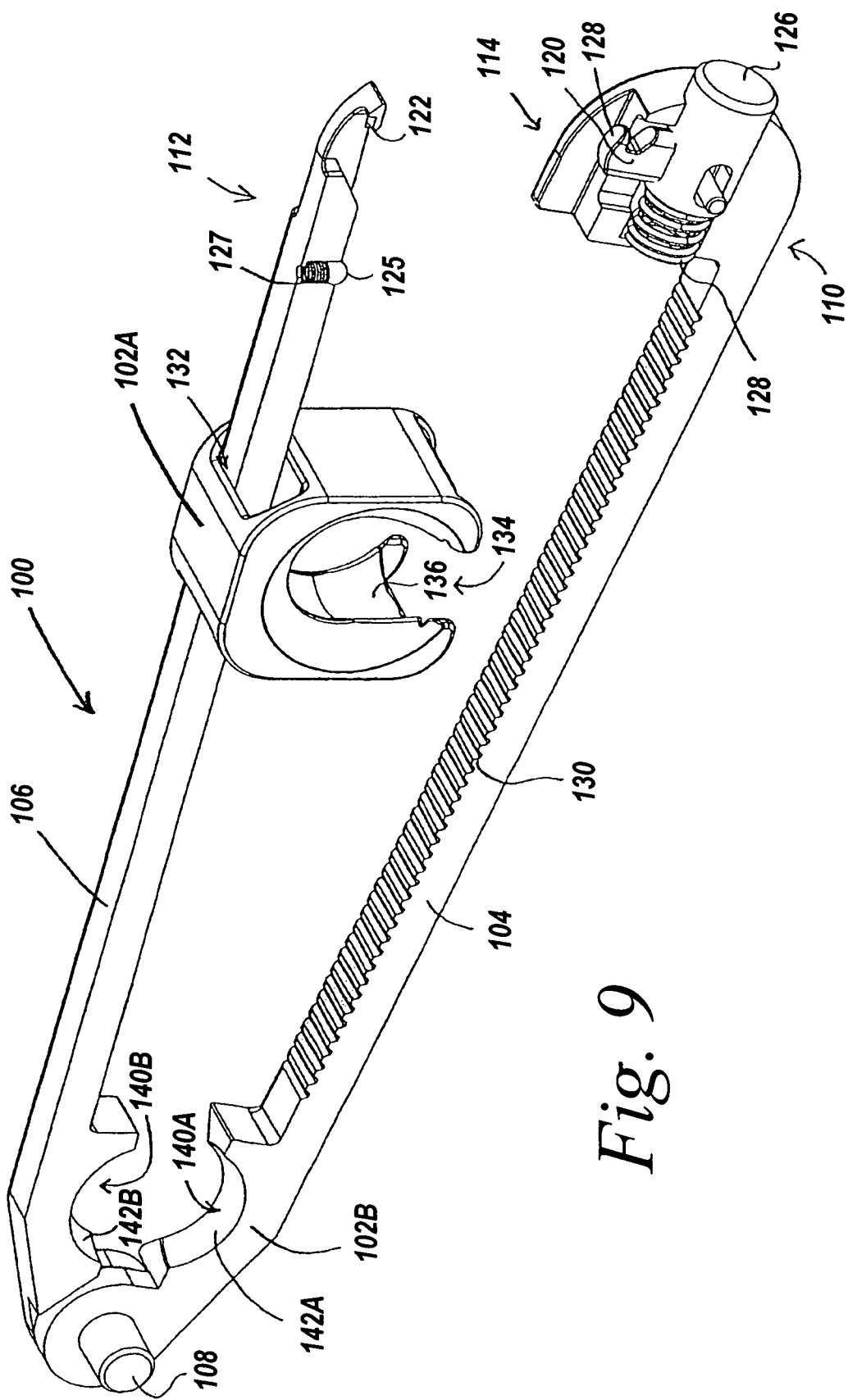
FIG. 9 is a partial cut away side view of the connector of FIG. 8, illustrating the connector in an open position.

The example connector 100 may include a first arm 104 pivotably connected to second arm 106 at a pivot point defined by a hinge pin 108. The example connector 100 may be movable between an open position in which the first end 110 of the first arm 104 is separated from the first end 112 of the second arm 106, as illustrated in FIGS. 8 and 9, and a closed position in which the first end 110 of the first arm 104 is coupled to the first end 112 of the second arm 106, as illustrated in FIGS. 8 and 9. The open position facilitates connection of the instruments to the receiving elements and adjustment of an adjustable receiving element, such as receiving element 102A. The example connector 100 may include a latch mechanism 114 for selective coupling the first end 110 of the first arm 104 to the first end 112 of the second arm 106. In the example embodiment, the latch mechanism 114 may include hook 120 positioned on the first arm 104 that may selectively engage a hook retaining element 122 positioned on the second arm 106. A cylindrically-shaped push button 126 is connected to the hook 122. Movement of the push button in a direction toward the hinge 108 causes the hook 120 to disengage from the hook retaining element 122 and, thus, releases the first arm 104 from the second arm 106. A spring 127 biases the push button 126 in a direction away from the hinge 108 and, thus, biases the hook 120 into an engagement position. The outer surface 128 of the hook 120 may be curved or angled to provide a camming surface that, when engaged by the bottom surface of the hook retaining element 122, causes the hook 120 to move from the engagement position toward the hinge 108, thus, allowing the hook 120 to engage the hook retaining element 122.

The first arm 104 and/or second arm 106 may include a retaining member for retaining the adjustable receiving elements 102 on the arms when the connector is in the open position. For example, the second arm 106 of the example connector 200 includes a retaining pin 125 for retaining the first receiving element 102A on the second arm 106. The retaining pin 125 may be adjusted along its axis between an extended position in which the pin 125 impedes motion of the receiving element along the arm 106 and retracted position that facilitates removal and placement of the receiving element 102 on the arm 106. A spring 127 may be provided to bias the pin 125 to the extended position.

The first receiving element 102A, in the example embodiment, includes a slot 132 for receiving the second arm 106 and permitting motion of the first receiving element 102A relative to the second arm 106 and other receiving elements, such as the second receiving element 102B. In the example embodiment, the first arm 104 includes a plurality of teeth 130 for engaging a plurality of teeth on one or more of the receiving elements, for example, the first receiving element 102A, when the connector 100 is in the closed position. The engagement of the teeth 130 with teeth provided on an adjustable receiving element, for example, the adjustable receiving element 102A, may inhibit motion of the adjustable receiving element, thereby fixing the adjustable receiving element in position relative to the first arm 104, the second arm 106, and the other receiving elements.

Figure 10:
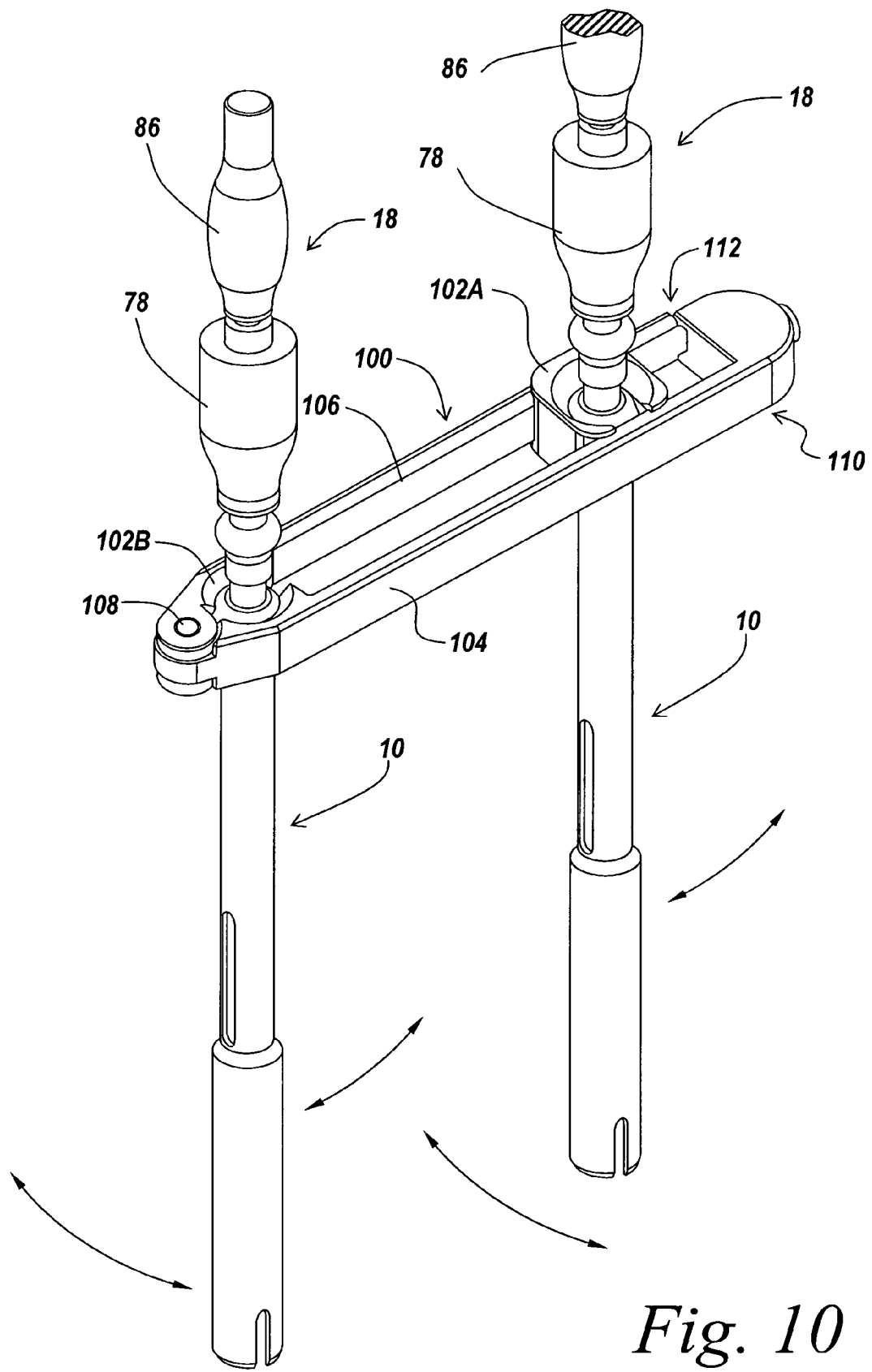
FIG. 10 is a perspective view of the connector of FIG. 8, illustrating the connector in the closed position and connecting two instruments such as the instrument of FIG. 1.
Figure 11:
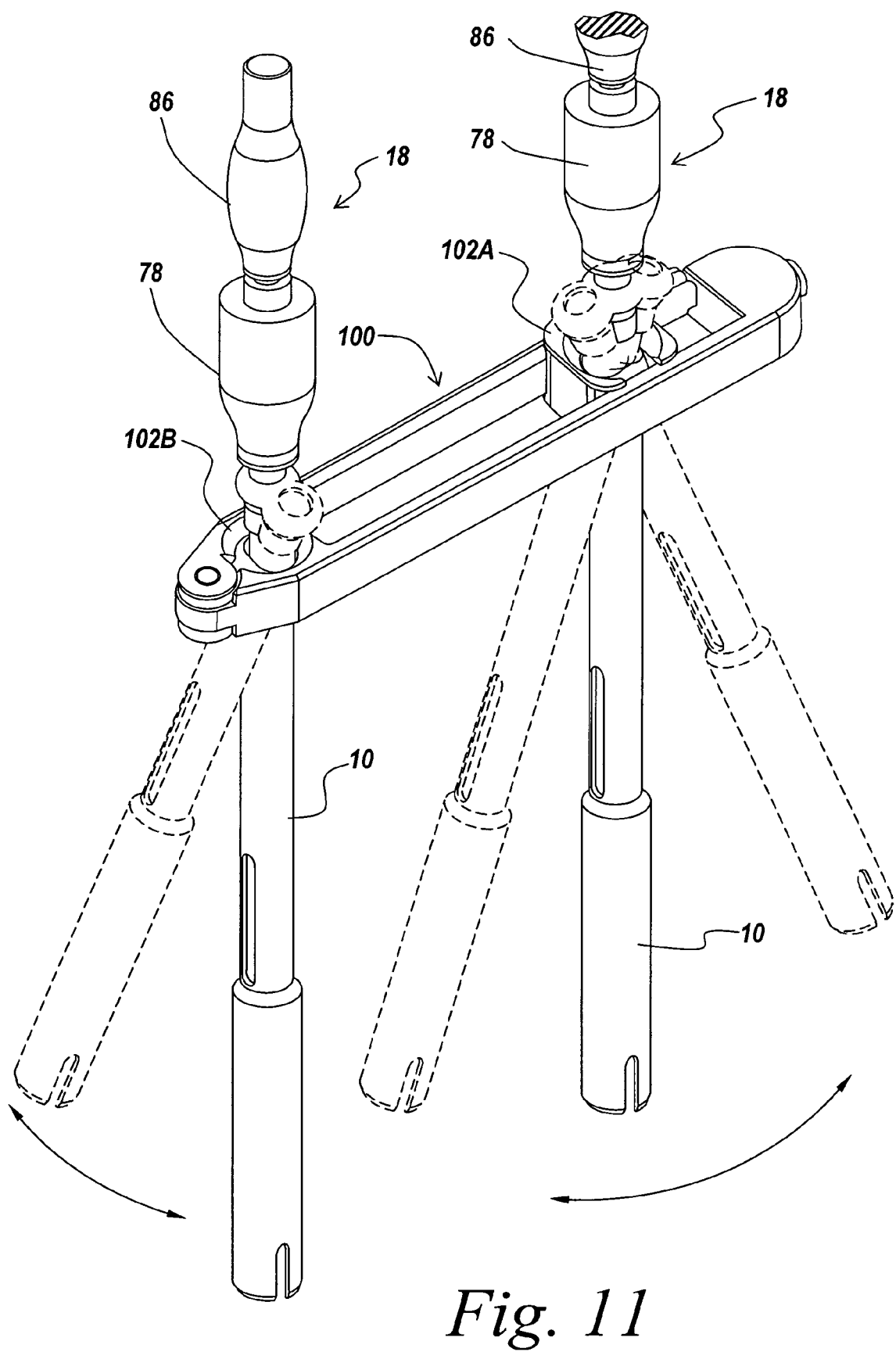
FIG. 11 is a perspective view of the connector of FIG. 8, illustrating the connector in the closed position and connecting two instruments such as the instrument of FIG. 1 wherein the connector can accommodate instruments in a number of different positions.

The first receiving element 102A is generally C-shaped having an opening 134 to facilitate positioning of an instrument within the receiving element 102A. The first arm 104 may be positioned across the opening 134 when the connector is in the closed position to retain the instrument in the first receiving element 102A. The first receiving element 102A may be configured to permit polyaxial motion of an instrument relative to the receiving element 102A and, thus, the connector 100. For example, the first receiving element 102A may include a generally spherically shaped surface 136 that defines a seat or engagement surface for the connection element of the instrument, for example, the connection element 32 of the example instrument 10, described above. The instrument 10, when connected to the first receiving element 102A of the connector 100, may be moved in a plurality of directions, for example, perpendicular to, parallel to, and about the axis of the instrument 10, as illustrated in FIGS. 10 and 11.

The second receiving element 102B, in the example embodiment, may be defined by a first arcuate surface 140A provided on the first arm 104 and a second arcuate surface 140B provided on the second arm 106. The first arcuate surface 140A may be spaced apart from the second arcuate surface 140B when the connector 100 is in the open position, as illustrated in FIGS. 8 and 9, to facilitate positioning of an instrument within the second receiving element 102B. When the connector 100 is in the closed position, as illustrated in FIGS. 10 and 11, the first arcuate surface 140A and the second arcuate surface 140B are spaced apart a distance sufficient to retain the instrument within the second receiving element 102B. The second receiving element 102B, like the first receiving element 102A, may be configured to permit polyaxial motion of an instrument relative to the receiving element 102B and, thus, the connector 100. For example, the first arcuate surface 140A and the second arcuate surface 140B may each have a partially spherically shaped surface 142A, 142B that cooperatively define a seat or engagement surface for the connection element of the instrument, for example, the connection element 32 of the example instrument 10, described above. The instrument 10, when connected to the second receiving element 102B of the connector 100, may be moved in a plurality of directions, for example, perpendicular to, parallel to, and about the axis of the instrument 10, as illustrated in FIGS. 10 and 11.

While the example embodiment of the connector 100 is described and illustrated as having two receiving elements, the number and type (i.e., fixed or adjustable) of receiving elements may be varied to accommodate the number of instruments desired to be connected. For example, the example connector 100, illustrated in FIGS. 13 and 14, includes three receiving elements—a fixed receiving element and two adjustable receiving elements.

Figure 12:
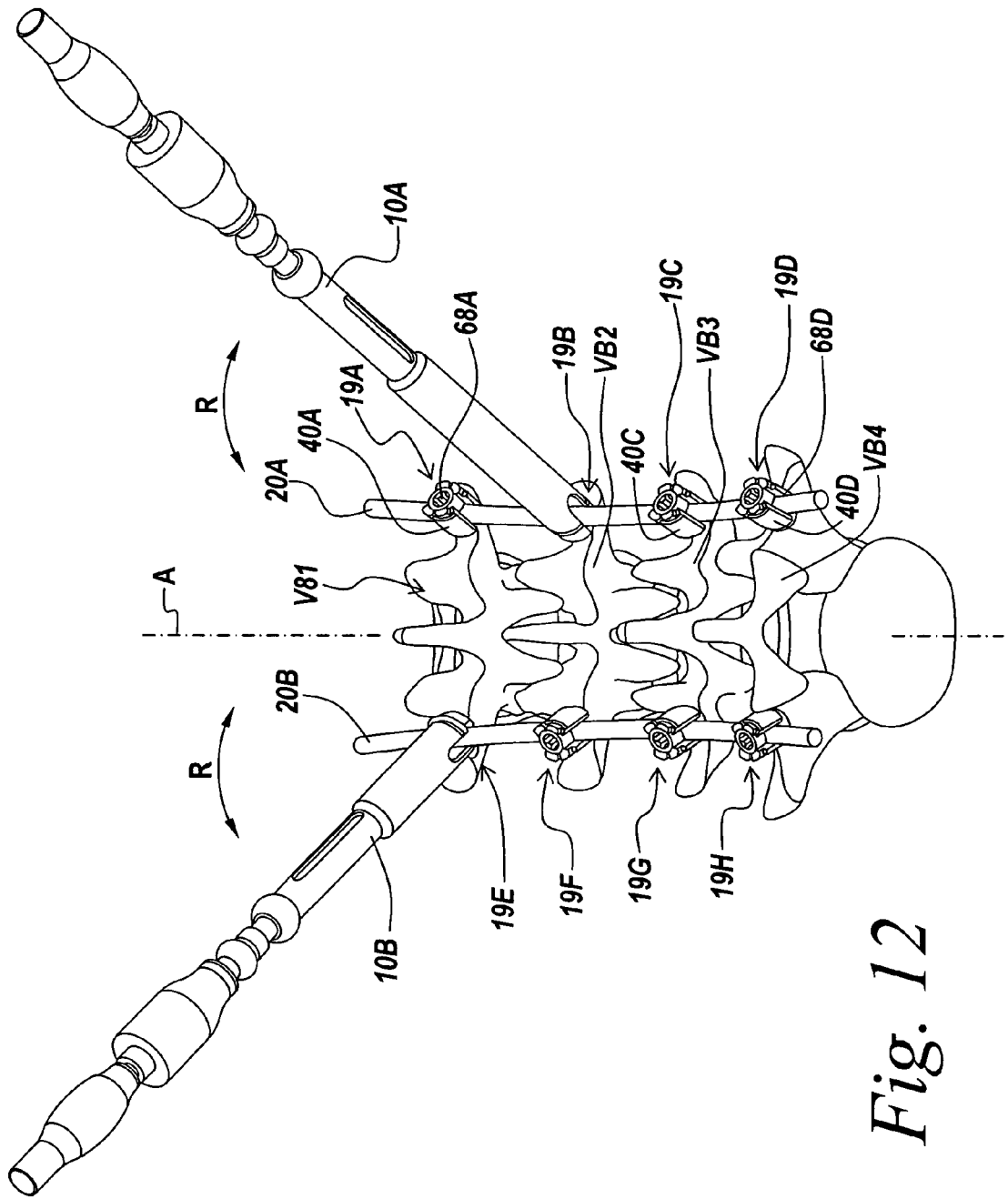
FIG. 12 is a perspective view of a first instrument connected to a first bone anchor engaged to a first vertebra and a second instrument connected to a second bone anchor engaged to a second vertebra, illustrating a method of adjusting the first vertebra relative to the second vertebra.

The example instrument 10 may be employed to manipulate a bone anchor and the vertebra in which the bone anchor is implanted. In one example method of manipulating a vertebra, the instrument 10 may be coupled to the receiving member or other portion of a bone anchor. Referring to FIG. 12, for example, a first instrument 10A may be coupled to the receiving member 40 of a bone anchor 19.

In the example method, a spinal construct including a plurality of bone anchors implanted in a plurality of vertebra and a spinal rod connecting the bone anchors may be positioned in advance of using the first instrument to manipulate a vertebra. For example, a first bone anchor 19A may be connected to a first vertebra VB1, a second bone anchor 19B may be connected to a second vertebra VB2, a third bone anchor 19C may be connected to a third vertebra VB3, and a fourth vertebra 18D may be connected to a fourth vertebra VB4. In the example method, the first, second, third, and fourth vertebrae are adjacent one another. In other example methods, the bone anchors may be connected to non-adjacent vertebra to create the spinal construct. The bone anchors may be implanted into any suitable portion of the vertebrae. In the example method, for example, each bone anchor is implanted into a pedicle of the vertebra.

A spinal fixation element 20A may be positioned relative to the bone anchors. For example, the spinal fixation element may be positioned in or proximate to the receiving member 40 of each bone anchor 19.

In certain example embodiments, a second construct may be positioned on the contra-lateral side of the spine from the first construct. In the example method, a fifth bone anchor 19E is connected to the first vertebra VB1 opposite the first bone anchor 19A, a sixth bone anchor 19F is connected to the second vertebra VB2 opposite the second bone anchor 19B, a seventh bone anchor 19F is connected to the third vertebra VB3 opposite the third bone anchor 19C, and an eighth bone anchor 19G is connected to the fourth vertebra VB4 opposite the fourth bone anchor 19D. A second spinal fixation element 20B may be connected to the bone anchors 18E-G.

One skilled in the art will appreciate that the constructs illustrated in the FIGS. are example constructs for facilitating the description of the use of the instruments and methods described herein. Other constructs employing the same or different bone anchors and fixation elements may be employed without departing from the scope of the present invention.

After connecting the first instrument 10A, the first instrument 10A may be manipulated to maneuver the second bone anchor 19B and the second vertebra VB2 relative to the first vertebra VB1, third vertebra VB3, and the fourth vertebra VB4. For example, the first instrument 10A may be moved a direction about the axis A of the spine, as indicated by arrow R in FIG. 12, to rotate the second vertebra VB2 about the axis A of the spine. Moreover, the instrument 10 may be used to maneuver the second bone anchor 19B and the second vertebra VB2 in any direction.

In the example method, a second instrument 10B may be connected to the fifth bone anchor 19E, which is connected to the first vertebra VB1. The second instrument 10B and the first instrument 10A may be manipulated to maneuver the first vertebra VB1 and the second vertebra VB2 relative to one another. For example, the first instrument 10A may be rotated about the axis A of the spine to rotate the second vertebra VB2 about the spine and the second instrument 10B may be rotated about the axis A of the spine to rotate the first vertebra VB1 about the axis A of the spine. The first instrument 10A and the second instrument 10B may provide counter-torque to one another to facilitate motion of the first and second vertebrae. For example, the first instrument 10A and the second instrument 10B may be rotated in opposite directions about the axis A of the spine to facilitate correction of the angular orientation of the second vertebra VB2 and the first vertebra VB1.

In the example method, a reduction element 18 may be inserted through the lumen 26 of the shaft 12 of the first instrument 10A to effect reduction or insertion of a closure mechanism 68 for the second bone anchor 19B.

Figure 13:
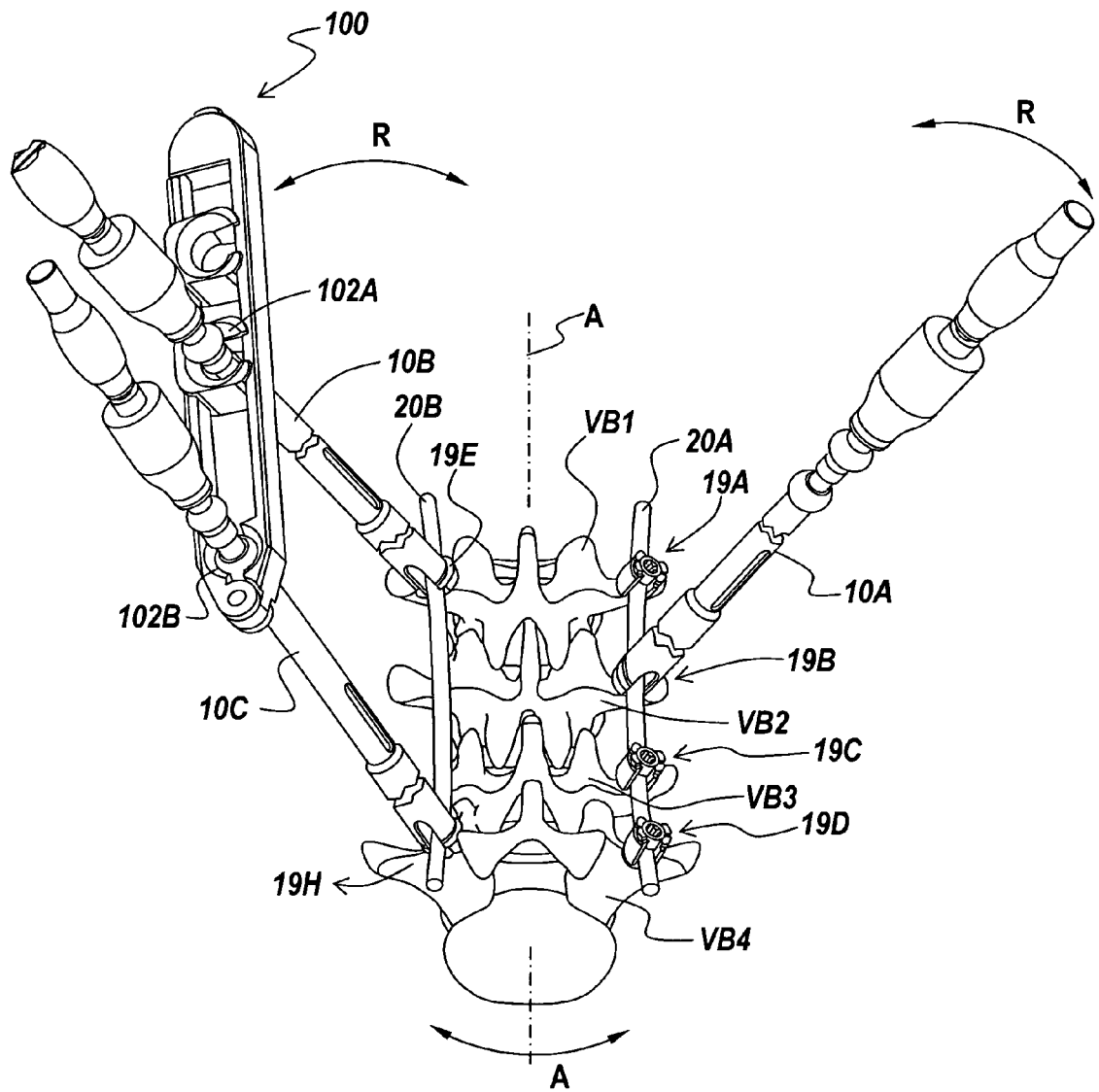
FIGS. 13 and 14 are perspective views of a connector connecting a first instrument to a second instrument, illustrating a method of adjusting a first and third vertebra relative to a second vertebra.
Figure 14:
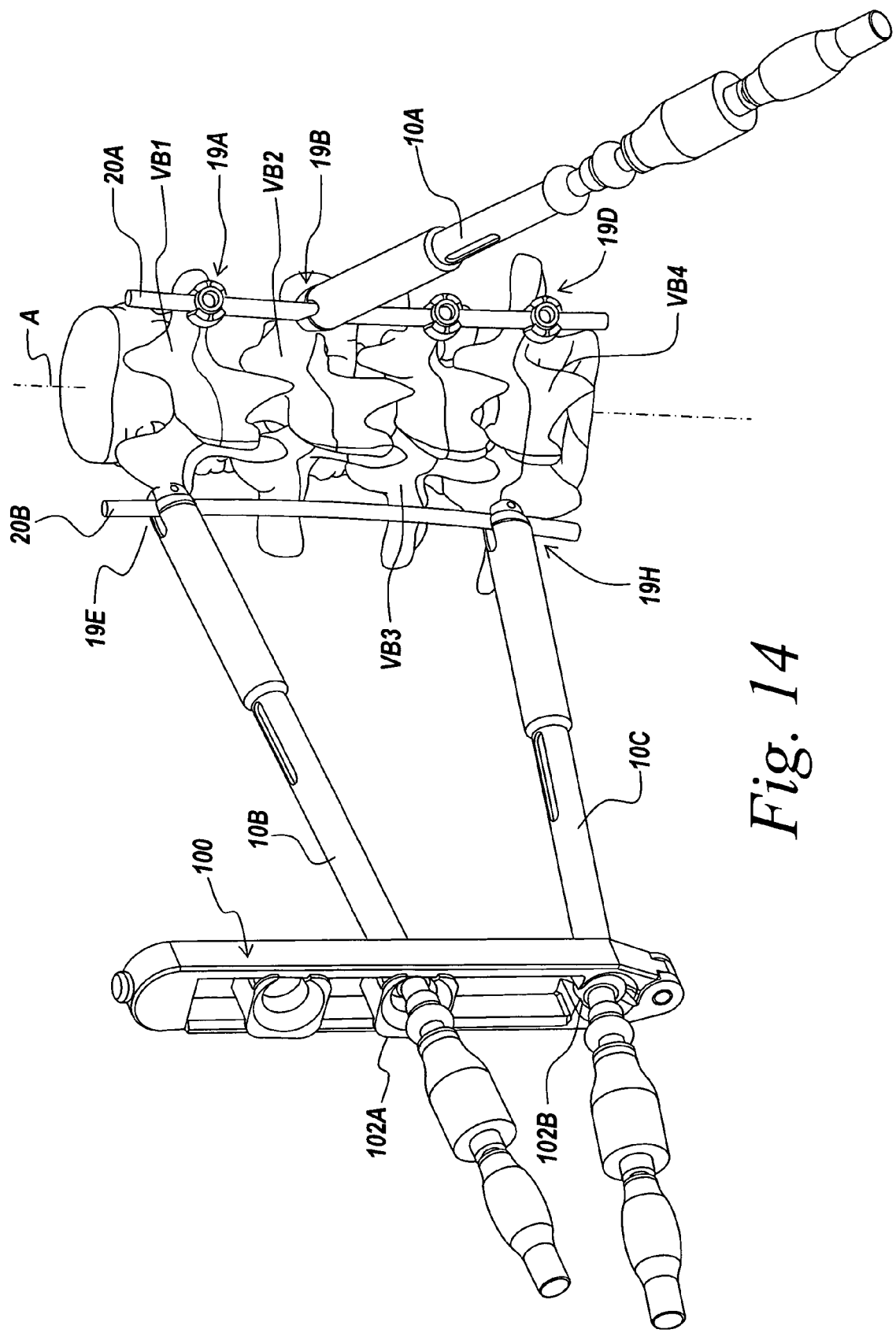

FIGS. 13 and 14 illustrate an example method for manipulating a plurality of vertebrae. In the example method, a first instrument 10A may be connected to a bone anchor 19B connected to a second vertebra. In addition, a second instrument 10B may be connected to a bone anchor 19E connected to a first vertebra and a third instrument 10C may be connected to a bone anchor 19H connected to a fourth vertebra VB4. The second and third instruments 10B, 10C may be connected by a connector, such as the connector 100 described above. After connecting the second and third instruments 10B, 10C to the respective bone anchor, the first receiving element 102A may be adjusted relative to the second receiving element 102B to facilitate connection of the second instrument 10B to the first receiving element 102A and the third instrument 10C to the second receiving element 102B. The connector 100 may be moved to manipulate the second instrument 10B and the third instrument 10C to rotate the first vertebra VB1 and the fourth vertebra VB4 relative to one another. For example, the connector 100 may be rotated in a direction indicated by arrow R about the axis A to rotate the first vertebra VB1 and the fourth vertebra VB2 about the axis A of the spine and relative to the second vertebra VB2 and the third vertebra VB3. Moreover, the first instrument 10A may be rotated in cooperation with the connector 100 to rotate the second vertebra VB2 about the axis A of the spine. The connector 100, and the second instrument 10B and third instrument 10C connected thereto, and the first instrument 10A may provide counter torque to one another. For example, the connector 100 and the first instrument 10A may be rotated in opposite directions about the axis A of the spine to facilitate correction of the angular orientation of the first vertebra VB1, the second vertebra VB2, and the fourth vertebra VB4.

Figure 15:
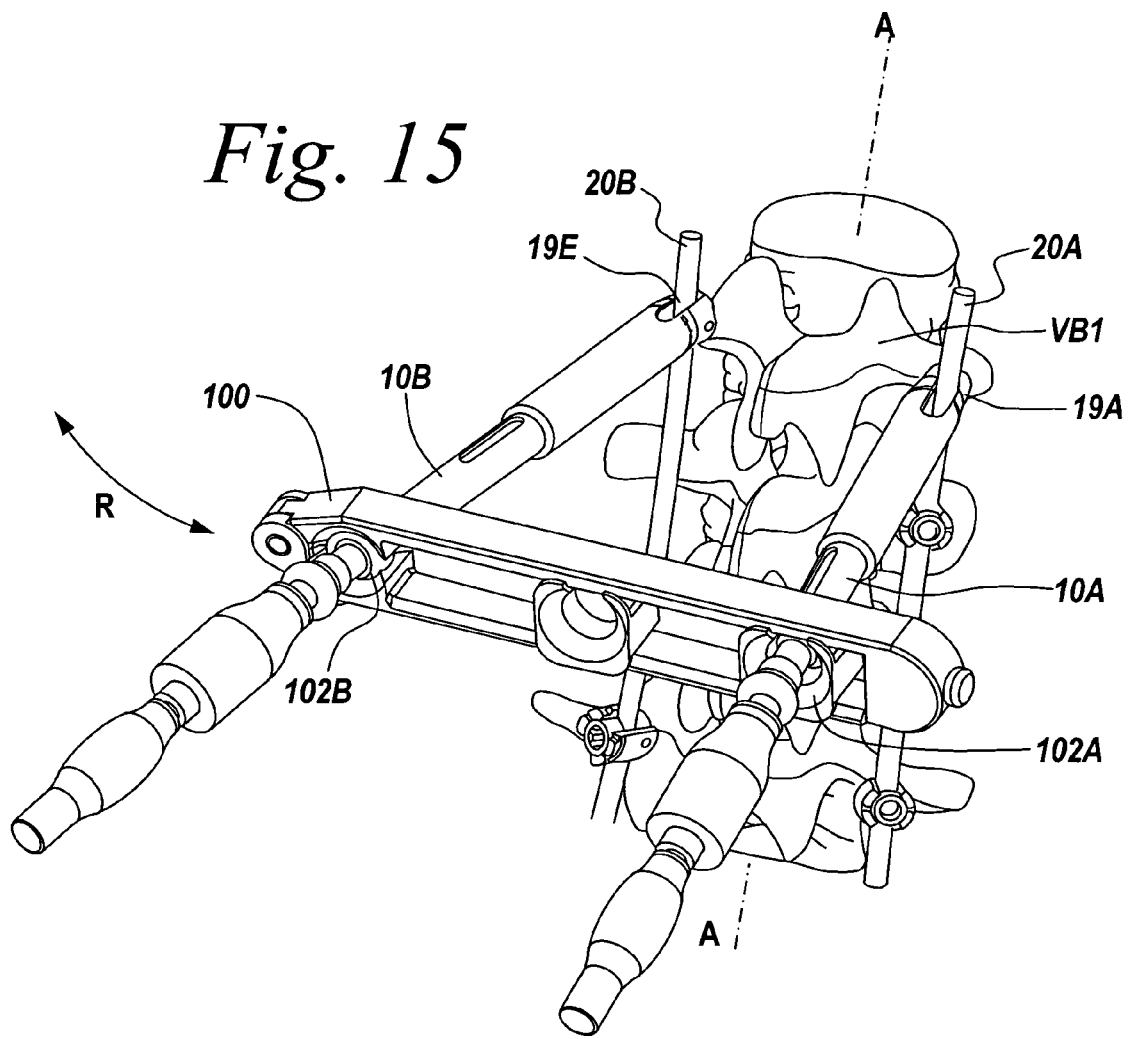
FIG. 15 is a perspective view of a connector connecting a first instrument to a second instrument wherein the first and second instruments are attached laterally to the same vertebra, illustrating a method of the vertebra.

FIG. 15 illustrates an example method for rotating a single vertebra by attaching instruments to bone anchor that inserted laterally into the same vertebra. In the example method, a first instrument 10A may be connected to a bone anchor 19A connected to a first vertebra VB1. In addition, a second instrument 10B may be connected to a bone anchor 19E connected to the first vertebra VB1 laterally from bone anchor 19A. The first and second instruments 10A and 10B may be connected by a connector, such as the connector 100 described above. After connecting the first and second instruments 10A, 10B to the respective bone anchor, the first receiving element 102A may be adjusted relative to the second receiving element 102B to facilitate connection of the first instrument 10A to the first receiving element 102A and the second instrument 10B to the second receiving element 102B. The connector 100 may be moved to manipulate the first instrument 10A and the second instrument 10B to rotate the first vertebra VB1. For example, the connector 100 may be rotated in a direction indicated by arrow R about the axis A to rotate the first vertebra VB1 about the axis A of the spine.

Figure 16:
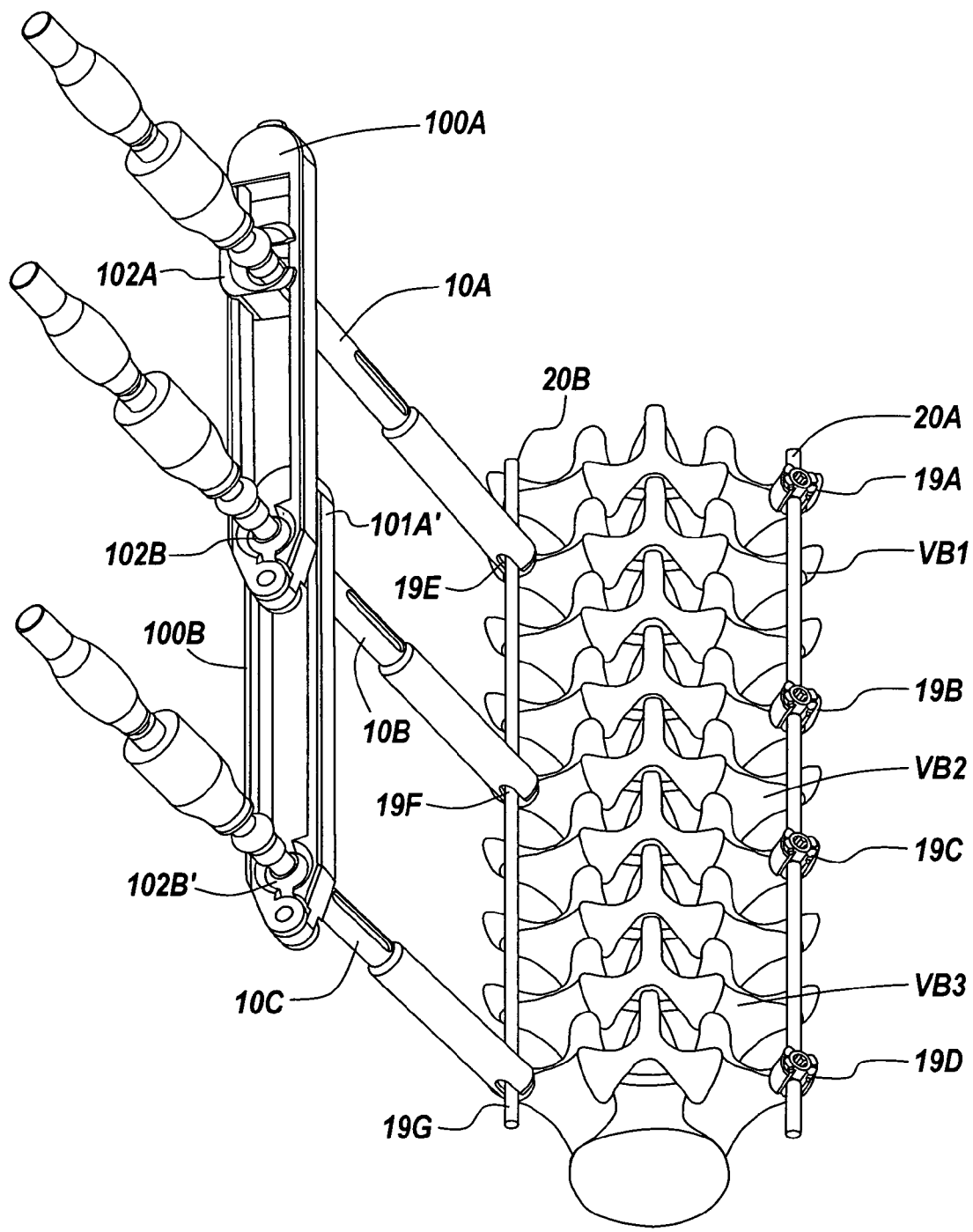
FIG. 16 is a perspective view of multiple connectors being used to connect multiple instruments.

FIG. 16 illustrates an example method for manipulating a plurality of vertebrae connected using multiple connectors. In the example method, a first instrument 10A may be connected to a bone anchor 19E connected to a first vertebra VB1. In addition, a second instrument 10B may be connected to a bone anchor 19F connected to a second vertebra VB2 and a third instrument 10C may be connected to a bone anchor 19G connected to a third vertebra VB3. The first and second instruments 10A, 10B may be connected by a first connector 100A. The first receiving element 102A of the first connector 100A may be adjusted relative to the second receiving element 102B of the first connector 100A to facilitate connection of the first instrument 10A to the first receiving element 102A and the second instrument 10B to the second receiving element 102B.

The second and third instrument 10B, 10C may then be connected by a second connector 100B. The first receiving element 102A' of the second connector 100B may be adjusted relative to the second receiving element 102B' of the second connector 100B to facilitate connection of the second instrument 10B to the first receiving element 102A' and the third instrument 10C to the second receiving element 102B'. This in turns connects the third instrument 10C to the first instrument 10A as the second instrument 10B is connected to both the first connector 100A and the second connector 100B. The connectors 100A and 100B may then be moved to manipulate the first instrument 10A, second instrument 10B, and the third instrument 10C to rotate the first vertebra VB1, second vertebra VB2 and the third vertebra VB3 relative to one another.

While the instruments and methods of the present invention have been particularly shown and described with reference to the example embodiments thereof, those of ordinary skill in the art will understand that various changes may be made in the form and details herein without departing from the spirit and scope of the present invention. Those of ordinary skill in the art will recognize or be able to ascertain many equivalents to the example embodiments described specifically herein by using no more than routine experimentation.

Such equivalents are intended to be encompassed by the scope of the present invention and the appended claims.

What is claimed is:

1. An instrument for manipulating and a bone anchor and a spinal fixation element offset from the bone anchor, the instrument comprising:
   a shaft having a proximal end, a distal end, and a lumen extending between the proximal end and the distal end,
   one or more fingers disposed at the distal end of the shaft configured to engage a spinal fixation element receiving member of a bone anchor and defining a slot for receiving a spinal fixation element offset from the spinal fixation element receiving member;
   an outer sleeve disposed about the shaft and configured to slide over the distal end of the shaft between a first position and a second position, when the outer sleeve is in the first position, the one or more fingers are unconstrained by the outer sleeve allowing the one or more fingers to receive the spinal fixation element in the slot and engage the spinal fixation element receiving member, when the outer sleeve is in the second position, the one or more fingers are constrained by the outer sleeve securing the spinal fixation element in the slot and the engagement of the spinal fixation element receiving member of the bone anchor by the one or more fingers to permit manipulation of the spinal fixation element and bone anchor by the instrument; and
   a reduction element configured to pass through the lumen of the shaft and engage the offset spinal fixation element to reduce the offset spinal fixation element into the spinal fixation element receiving member of the bone anchor, the reduction element being configured to insert a closure mechanism into the bone anchor to restrict motion of the spinal fixation element relative to the bone anchor,
   wherein the shaft comprises a plurality connection elements each being configured to engage a connector for connecting the instrument to another instrument,
   wherein the outer sleeve comprises a second slot corresponding to the slot defined by the one or more fingers, the second slot being configured to receive the spinal fixation element that is offset from the spinal fixation element receiving member when the outer sleeve is in the second position.

2. The instrument of claim 1, wherein the outer sleeve includes a slot for receiving the spinal fixation element offset from the spinal fixation element receiving member.

3. The instrument of claim 1, wherein the outer sleeve can be slid over the distal end of the inner shaft to a third position in which the outer sleeves reduces the offset spinal fixation element into the spinal fixation element receiving member of the bone anchor.

4. The instrument of claim 1, wherein the connection element is configured to permit polyaxial motion of the instrument relative to the connector.

5. The instrument of claim 1, wherein the lumen of the shaft includes inner threads for engaging corresponding threads on the reduction element passing through the lumen of the shaft.

6. The instrument of claim 1, wherein the instrument is further configured to insert a locking mechanism into the bone anchor to secure the spinal fixation element to the bone anchor.

7. A system for manipulating one or more vertebrae, the system comprising:
   a first instrument comprising:
      a shaft having a proximal end, a distal end, and a lumen extending between the proximal end and the distal end,
      one or more fingers disposed at the distal end of the shaft configured to engage a spinal fixation element receiving member of a bone anchor and defining a slot for receiving a spinal fixation element offset from the spinal fixation element receiving member;
      an outer sleeve disposed about the shaft and configured to slide over the distal end of the shaft between a first position and a second position, when the outer sleeve is in the first position, the one or more fingers are unconstrained by the outer sleeve allowing the one or more fingers to receive the spinal fixation element in the slot and engage the spinal fixation element receiving member, when the outer sleeve is in the second position, the one or more fingers are constrained by the outer sleeve securing the spinal fixation element in the slot and the engagement of the spinal fixation element receiving member of the bone anchor by the one or more fingers to permit manipulation of the spinal fixation element and bone anchor by the instrument; and
      a reduction element configured to pass through the lumen of the shaft and engage the offset spinal fixation element to reduce the offset spinal fixation element into the spinal fixation element receiving member of the bone anchor, the reduction element being configured to insert a closure mechanism into the bone anchor to restrict motion of the spinal fixation element relative to the bone anchor;
   a second instrument comprising:
      a shaft having a proximal end, a distal end, and a lumen extending between the proximal end and the distal end,
      one or more fingers disposed at the distal end of the shaft configured to engage a spinal fixation element receiving member of a bone anchor and defining a slot for receiving a spinal fixation element offset from the spinal fixation element receiving member;
      an outer sleeve disposed about the shaft and configured to slide over the distal end of the shaft between a first position and a second position, when the outer sleeve is in the first position, the one or more fingers are unconstrained by the outer sleeve allowing the one or more fingers to receive the spinal fixation element in the slot and engage the spinal fixation element receiving member, when the outer sleeve is in the second position, the one or more fingers are constrained by the outer sleeve securing the spinal fixation element in the slot and the engagement of the spinal fixation element receiving member of the bone anchor by the one or more fingers to permit manipulation of the spinal fixation element and bone anchor by the instrument; and
      a reduction element configured to pass through the lumen of the shaft and engage the offset spinal fixation element to reduce the offset spinal fixation element into the spinal fixation element receiving member of the bone anchor, the reduction element being configured to insert a closure mechanism into the bone anchor to restrict motion of the spinal fixation element relative to the bone anchor; and
   a connector connecting the first instrument and the second instrument, the connector including a first receiving element for receiving the first instrument and a second receiving element for receiving the second instrument, the first receiving element being adjustable relative to the second receiving element,
wherein the shaft of the first instrument or the second instrument comprises a plurality connection elements each being configured to engage the connector for connecting the first instrument or the second instrument to another instrument,
wherein the outer sleeve of the first instrument or the second instrument comprises a second slot corresponding to the slot defined by the one or more fingers, the second slot being configured to receive the spinal fixation element that is offset from the spinal fixation element receiving member when the outer sleeve is in the second position.

8. The system of claim 7, wherein the first instrument is angularly adjustable relative to the first receiving member.

9. The system of claim 8, wherein the second instrument is angularly adjustable relative to the second receiving member.

10. A method of manipulating a bone anchor and spinal fixation element, the method comprising:
connecting a bone anchor to a vertebra;
positioning a spinal fixation element in proximity to a receiving member of the bone anchor;
connecting an instrument comprising:
a shaft having a proximal end, a distal end, and a lumen extending between the proximal end and the distal end,
one or more fingers disposed at the distal end of the shaft configured to engage a spinal fixation element receiving member of a bone anchor and defining a slot for receiving a spinal fixation element offset from the spinal fixation element receiving member;
an outer sleeve disposed about the shaft and configured to slide over the distal end of the shaft between a first position and a second position, when the outer sleeve is in the first position, the one or more fingers are unconstrained by the outer sleeve allowing the one or more fingers to receive the spinal fixation element in the slot and engage the spinal fixation element receiving member, when the outer sleeve is in the second position, the one or more fingers are constrained by the outer sleeve securing the spinal fixation element in the slot and the engagement of the spinal fixation element receiving member of the bone anchor by the one or more fingers to permit manipulation of the spinal fixation element and bone anchor by the instrument; and
a reduction element configured to pass through the lumen of the shaft and engage the offset spinal fixation element to reduce the offset spinal fixation element into the spinal fixation element receiving member of the bone anchor;
inserting a closure mechanism into the bone anchor using the reduction element, and manipulating the reduction element to tighten the closure mechanism to restrict motion of the spinal fixation element relative to bone anchor; and
manipulating the instrument to rotate the bone anchor and the spinal fixation element,
wherein the shaft comprises a plurality connection elements each being configured to engage a connector for connecting the instrument to another instrument,
wherein the outer sleeve comprises a second slot corresponding to the slot defined by the one or more fingers, the second slot being configured to receive the spinal fixation element that is offset from the spinal fixation element receiving member when the outer sleeve is in the second position.

11. The method of claim 10, further comprising engaging the spinal fixation element received in the slot with the reduction element, and manipulating the reduction element to reduce the spinal fixation element into the receiving member of the bone anchor.

12. The method of claim 10, further comprising:
connecting a second bone anchor to a second vertebra;
positioning the spinal fixation element in proximity to a receiving member of the bone anchor
connecting a second instrument to the receiving member of the second bone anchor, coupling a connector to the first instrument and to the second instrument, moving the connector to manipulate the first instrument and the second instrument to rotate the first vertebra, spinal fixation element, and the second vertebra relative to one another.

13. The method of claim 12, further comprising connecting a third bone anchor to a third vertebra, the third bone anchor positioned opposite the first bone anchor and the second bone anchor relative to an axis of the vertebrae, connecting a third instrument to the receiving member of the third bone anchor, and manipulating the connector and the third instrument to rotate the first vertebra and the second vertebra relative to the third vertebra.

14. The method of claim 13, wherein the third vertebra is interposed between the first vertebra and the second vertebra.

15. The method of claim 12, wherein the at least one of the first instrument and the second instrument is adjustable relative to the connector.

16. The method of claim 12, further comprising connecting a third bone anchor to a third vertebra, the third bone anchor positioned in line with the first and second bone anchors, coupling a second connector to the second instrument and to the third instrument; moving the first and second connectors to manipulate the first, second and third instrument to rotate the first vertebra, spinal fixation element, second vertebra, and third vertebra relative to one another.

17. The method of claim 10, further comprising:
connecting a second bone anchor to the first vertebra laterally from the first bone anchor;
connecting a second instrument to the receiving member of the second bone anchor, coupling a connector to the first instrument and to the second instrument, moving the connector to manipulate the first instrument and the second instrument to rotate the first vertebra.

18. The method of claim 17, further comprising positioning a second spinal fixation element in proximity to a receiving member of the second bone anchor prior to connecting the second instrument.

* * * * *